(12) United States Patent
Sutterlin, III

(10) Patent No.: US 9,549,764 B2
(45) Date of Patent: Jan. 24, 2017

(54) OCCIPITAL PLATE ASSEMBLIES WITH POLYAXIAL HEAD CONNECTORS

(71) Applicant: Chester E. Sutterlin, III, Longboat Key, FL (US)

(72) Inventor: Chester E. Sutterlin, III, Longboat Key, FL (US)

( * ) Notice: Subject to any disclaimer, the term of this patent is extended or adjusted under 35 U.S.C. 154(b) by 0 days.

(21) Appl. No.: 14/763,999

(22) PCT Filed: Jan. 29, 2014

(86) PCT No.: PCT/US2014/013682
§ 371 (c)(1),
(2) Date: Jul. 28, 2015

(87) PCT Pub. No.: WO2014/120834
PCT Pub. Date: Aug. 7, 2014

(65) Prior Publication Data
US 2015/0351812 A1 Dec. 10, 2015

Related U.S. Application Data

(60) Provisional application No. 61/849,553, filed on Jan. 29, 2013.

(51) Int. Cl.
*A61B 17/80* (2006.01)
*A61B 17/70* (2006.01)
*A61B 17/56* (2006.01)

(52) U.S. Cl.
CPC ....... *A61B 17/7035* (2013.01); *A61B 17/7037* (2013.01); *A61B 17/7044* (2013.01);
(Continued)

(58) Field of Classification Search
CPC ............ A61B 17/7049; A61B 17/7053; A61B 17/7055; A61B 17/7056
(Continued)

(56) References Cited

U.S. PATENT DOCUMENTS 5,346,492 A 9/1994 Morgan
5,360,429 A 11/1994 Jeanson et al.
(Continued)

FOREIGN PATENT DOCUMENTS

EP 0544384 A2 6/1993
EP 1928333 A1 6/2008
(Continued)

OTHER PUBLICATIONS

International Search Report dated Aug. 4, 2015 in corresponding PCT Application No. PCT/US2014/013682.
(Continued)

*Primary Examiner* — Ellen C Hammond
*Assistant Examiner* — Christina Negrellirodrigue
(74) *Attorney, Agent, or Firm* — Carter, DeLuca, Farrell & Schmidt, LLP

(57) ABSTRACT

Occipital plates and assemblies combining occipital plates with one of several types of spinal rods or cervical plates in a procedure to fuse a portion of a skull to a portion of a spine. An array of different occipital plates are disclosed, including options for making adjustments to the occipital plates by bending thinned portions of the occipital plates. The spinal rods engage polyaxial connector assemblies that are rotated posterior of the bony attachment section that provides an array of screw holes for affixing the occipital plate to the skull using at least one non-angled and non-articulated instrument. One or more holes for securing tensioning cables are provided in the occipital plates. Additional variations of these concepts are disclosed. Methods of using the disclosed components in surgical procedures are disclosed.

20 Claims, 20 Drawing Sheets

(52) U.S. Cl.
CPC ...... *A61B 17/7055* (2013.01); *A61B 17/7059* (2013.01); *A61B 17/8085* (2013.01); *A61B 17/7053* (2013.01); *A61B 2017/564* (2013.01)

(58) Field of Classification Search
USPC .................................. 606/70, 71, 280–299
See application file for complete search history.

(56) References Cited

U.S. PATENT DOCUMENTS

| | | | |
|---|---|---|---|
| 5,364,399 | A | 11/1994 | Lowery et al. |
| 5,545,164 | A | 8/1996 | Howland |
| 6,146,382 | A | 11/2000 | Hurlbert |
| 6,293,949 | B1 | 9/2001 | Justis et al. |
| 6,524,315 | B1 | 2/2003 | Selvitelli et al. |
| 6,547,790 | B2 | 4/2003 | Harkey, III et al. |
| 6,902,565 | B2 | 6/2005 | Berger et al. |
| 7,115,142 | B2 | 10/2006 | Muhanna et al. |
| 7,232,441 | B2 | 6/2007 | Altarac et al. |
| 7,341,601 | B2 | 3/2008 | Eisermann et al. |
| 7,572,282 | B2 | 8/2009 | Boomer et al. |
| 7,575,588 | B2 | 8/2009 | Barker et al. |
| 7,621,942 | B2 | 11/2009 | Piehl |
| 7,695,500 | B2 | 4/2010 | Markworth |
| 7,776,070 | B2 | 8/2010 | Null et al. |
| 7,824,433 | B2 | 11/2010 | Williams |
| 7,901,433 | B2 | 3/2011 | Forton et al. |
| 8,182,511 | B2 | 5/2012 | Henderson et al. |
| 8,187,302 | B2 | 5/2012 | Henderson, Sr. et al. |
| 8,226,695 | B2 | 7/2012 | Moore et al. |
| 8,246,662 | B2 | 8/2012 | Lemoine et al. |
| 8,337,496 | B2 | 12/2012 | Piehl |
| 8,348,981 | B2 | 1/2013 | Cheema et al. |
| 8,394,131 | B2 | 3/2013 | Wing et al. |
| 8,403,965 | B2 * | 3/2013 | Henderson .......... A61B 17/7047 606/280 |
| 8,556,939 | B2 | 10/2013 | Henderson et al. |
| 8,556,942 | B2 | 10/2013 | Ziolo et al. |
| 8,845,697 | B2 | 9/2014 | Montello et al. |
| 8,858,470 | B2 | 10/2014 | Henderson et al. |
| 8,986,351 | B2 * | 3/2015 | Gephart ................ A61B 17/70 606/246 |
| 9,107,717 | B2 | 8/2015 | Henderson, Sr. et al. |
| 2009/0024147 | A1 | 1/2009 | Ralph et al. |
| 2009/0048675 | A1 | 2/2009 | Bhatnagar et al. |
| 2010/0036429 | A1 | 2/2010 | Buck |
| 2010/0094351 | A1 * | 4/2010 | Haggenmaker .... A61B 17/7055 606/286 |
| 2010/0160964 | A1 | 6/2010 | Malek |
| 2011/0106081 | A1 | 5/2011 | Graham et al. |
| 2011/0106085 | A1 | 5/2011 | Null et al. |
| 2013/0238033 | A1 * | 9/2013 | Black ................ A61B 17/7053 606/286 |
| 2013/0253516 | A1 * | 9/2013 | Mackall ............ A61B 17/7059 606/70 |
| 2014/0277503 | A1 | 9/2014 | Mendel et al. |
| 2015/0238237 | A1 | 8/2015 | Madjarov |
| 2015/0289911 | A1 | 10/2015 | Beyar et al. |

FOREIGN PATENT DOCUMENTS

| | | |
|---|---|---|
| WO | 02067791 | 9/2002 |
| WO | 2009061604 A1 | 5/2009 |
| WO | 2012135860 A2 | 10/2012 |
| WO | 2012138852 A1 | 10/2012 |
| WO | 2014120834 A1 | 8/2014 |

OTHER PUBLICATIONS

Patent Examination Report issued in Australian Patent Application No. 2014212444 dated Jun. 11, 2016.
Annex to European Search Report issued in European Patent Application No. EP 14746503 on Sep. 26, 2016, 7 pages.

* cited by examiner

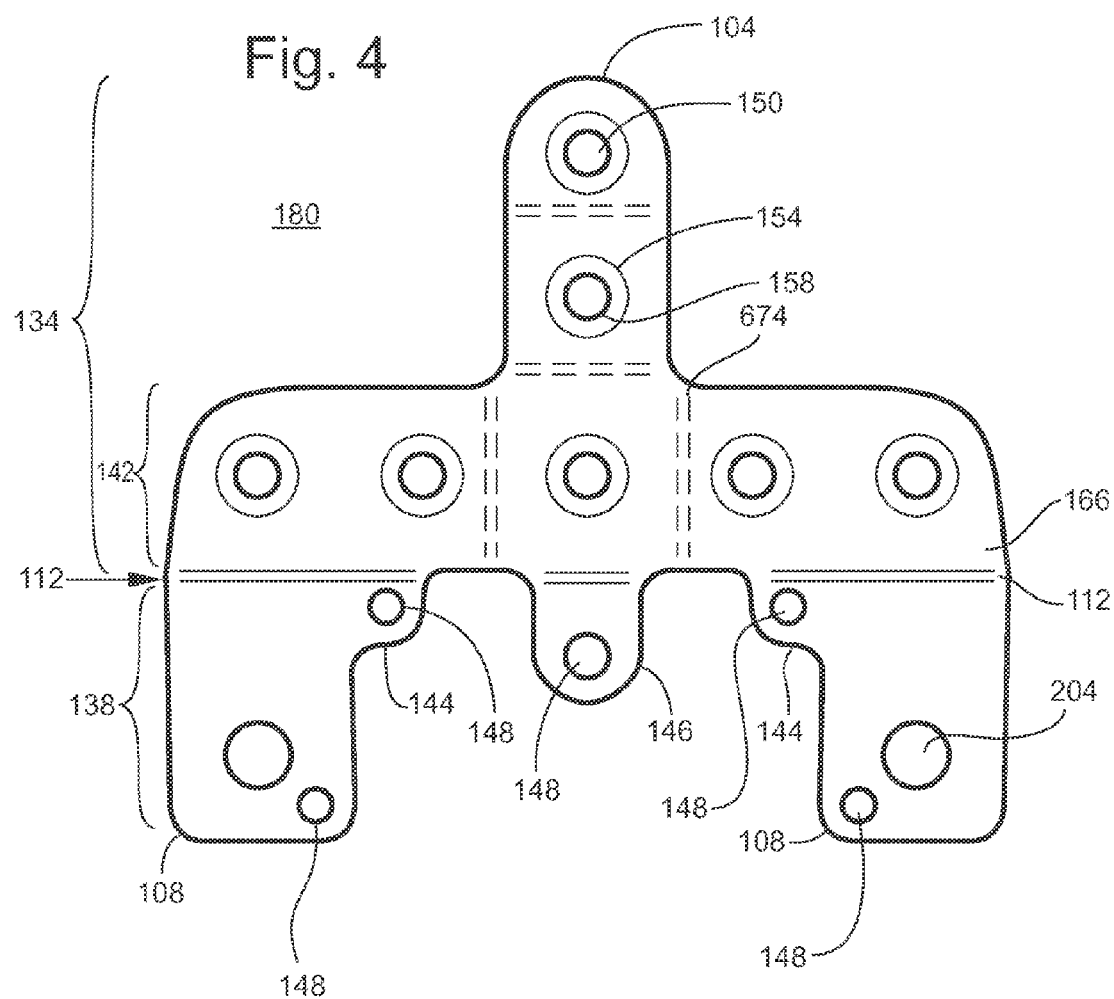

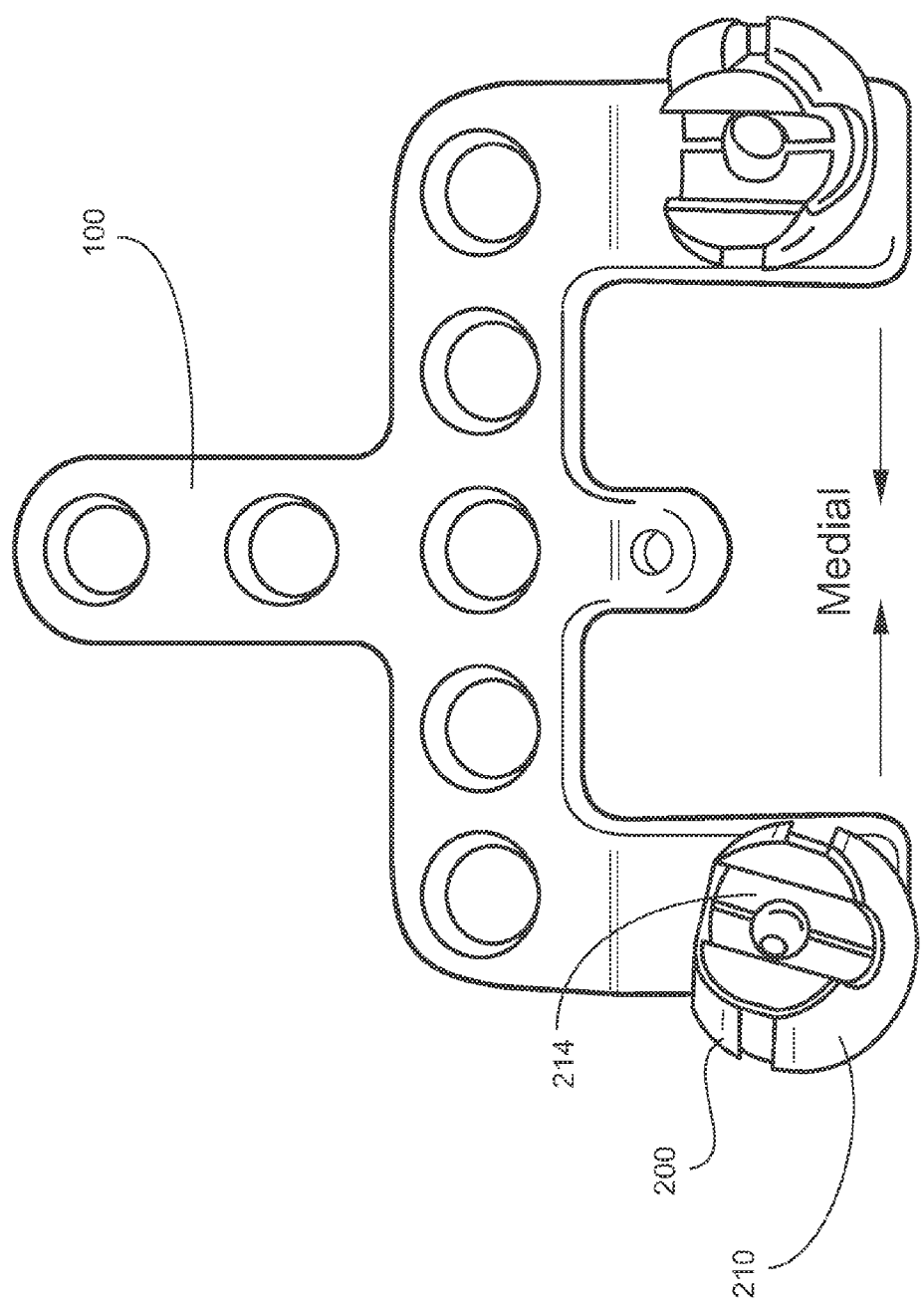

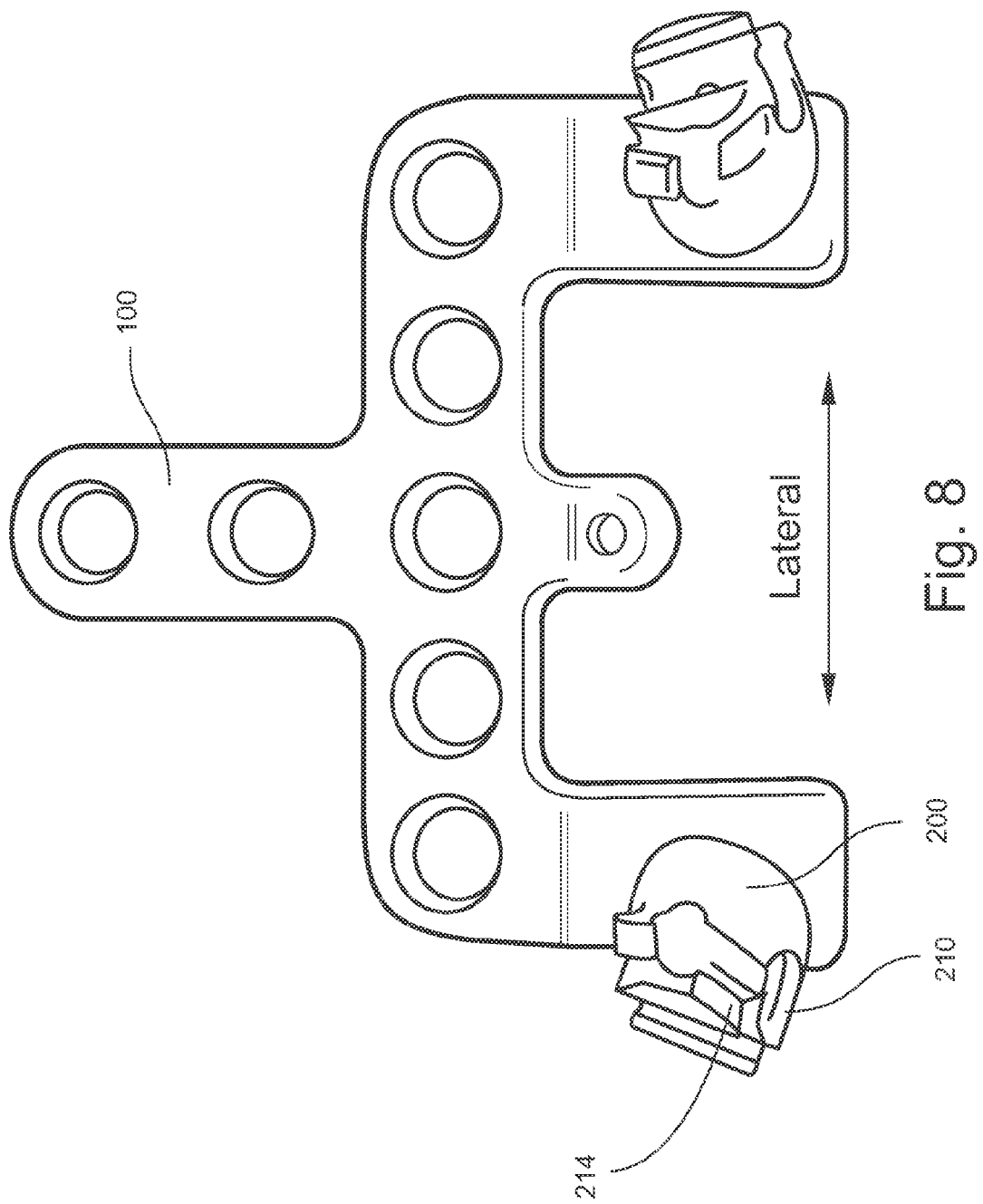

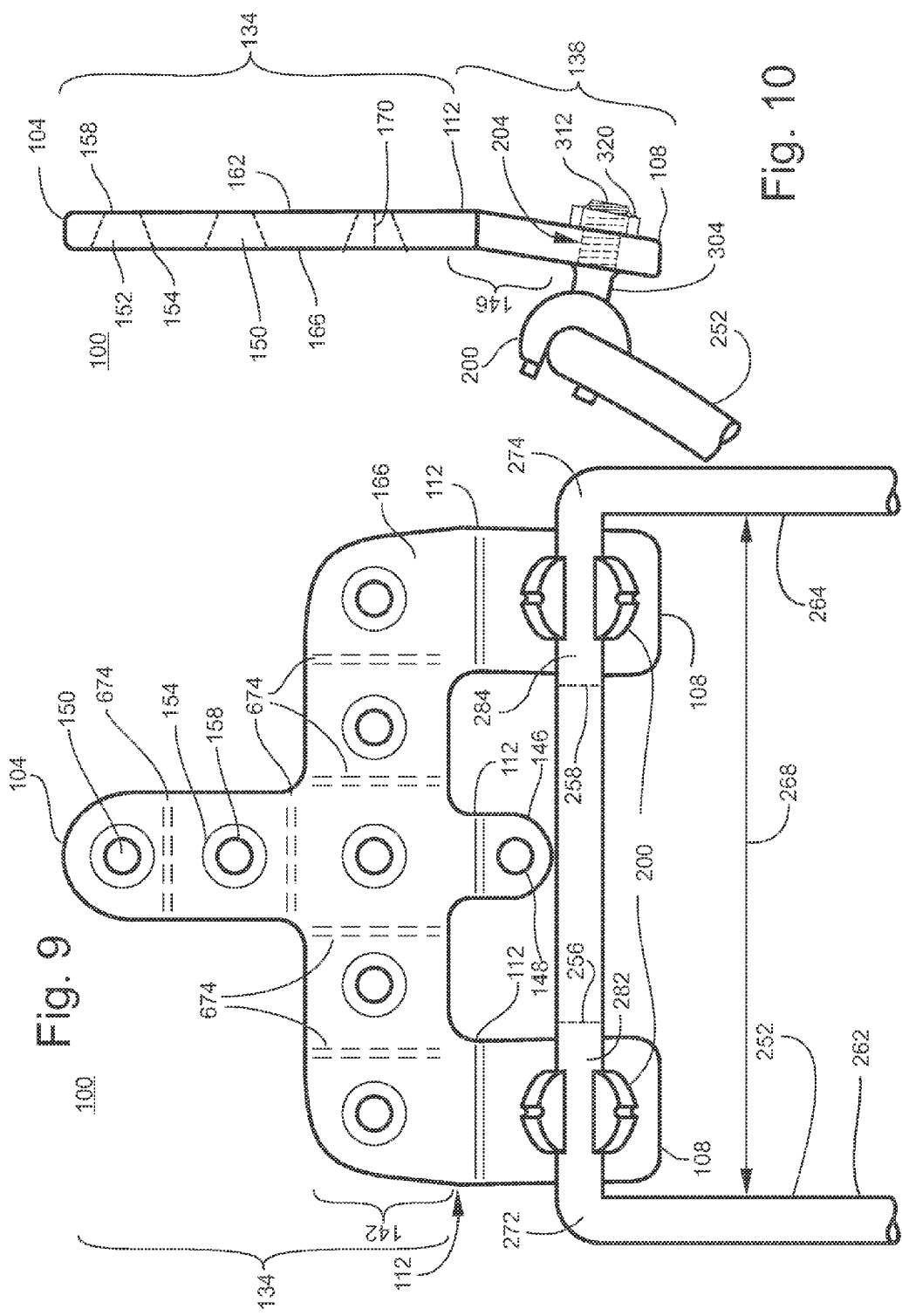

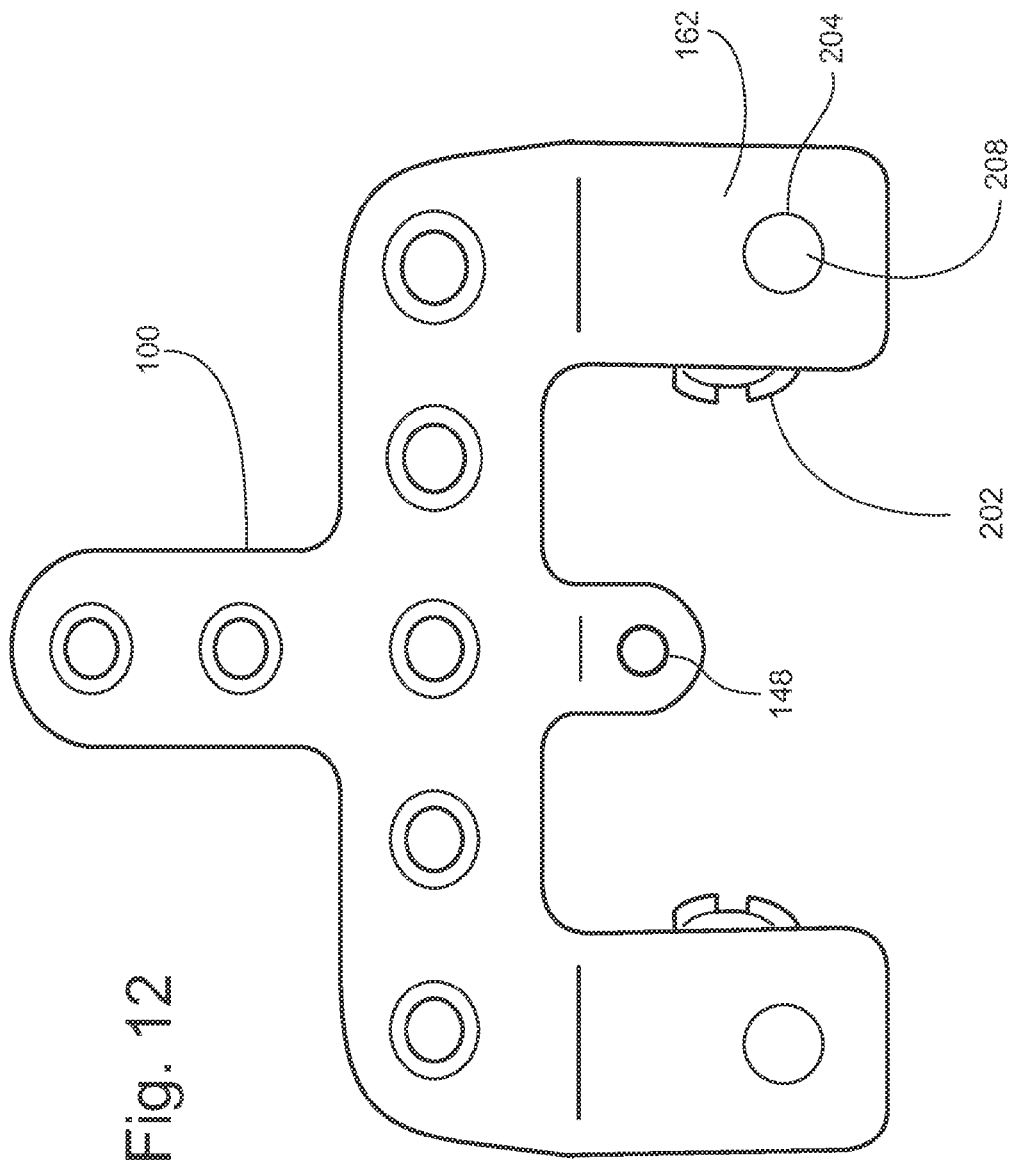

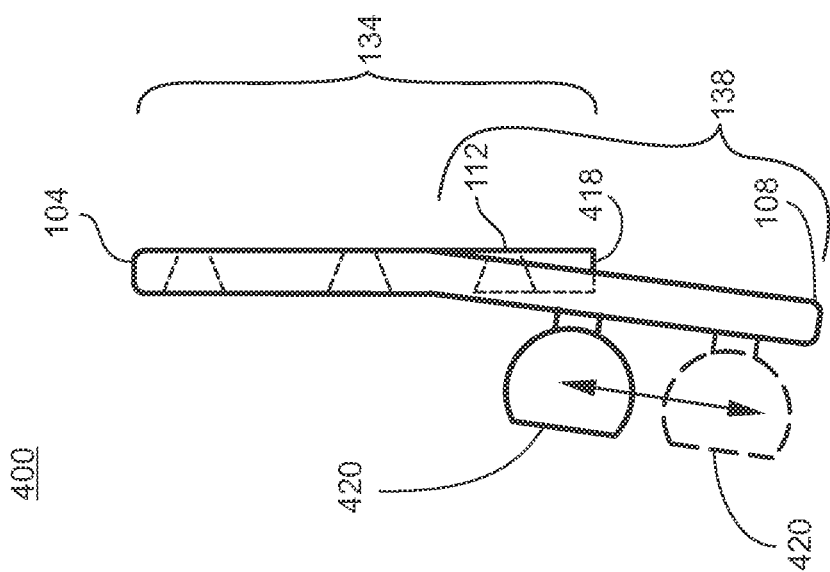
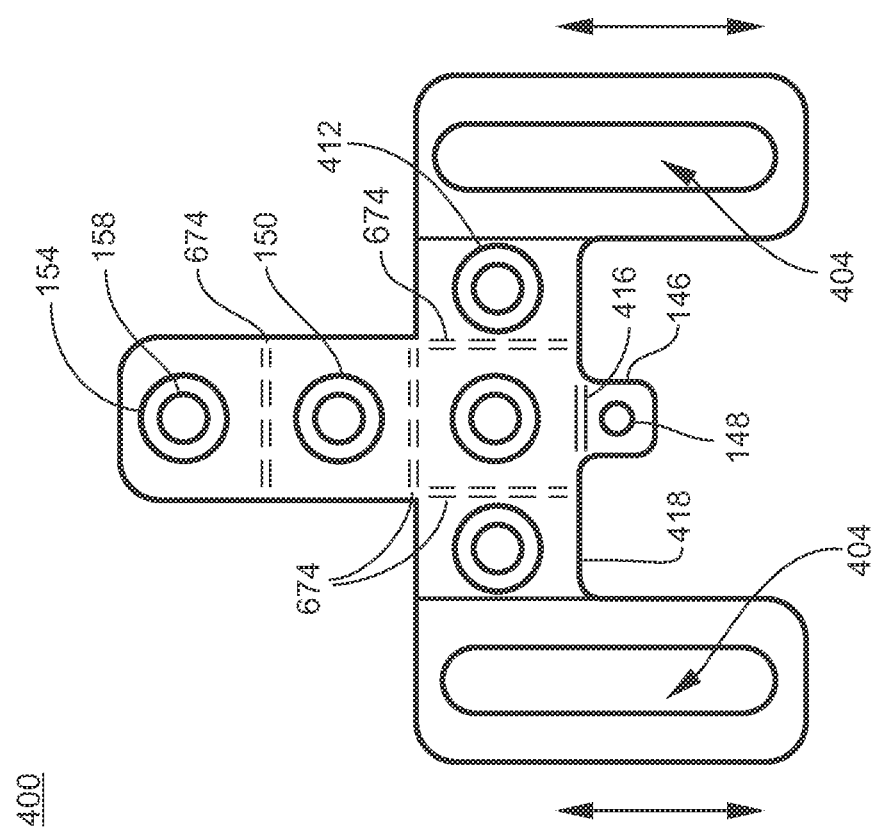

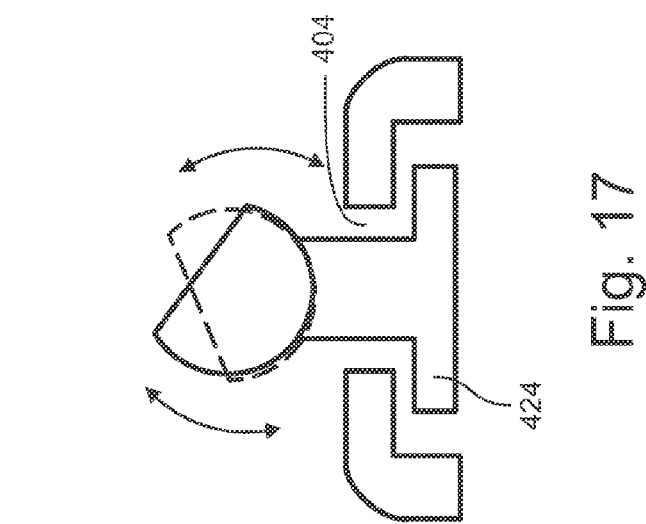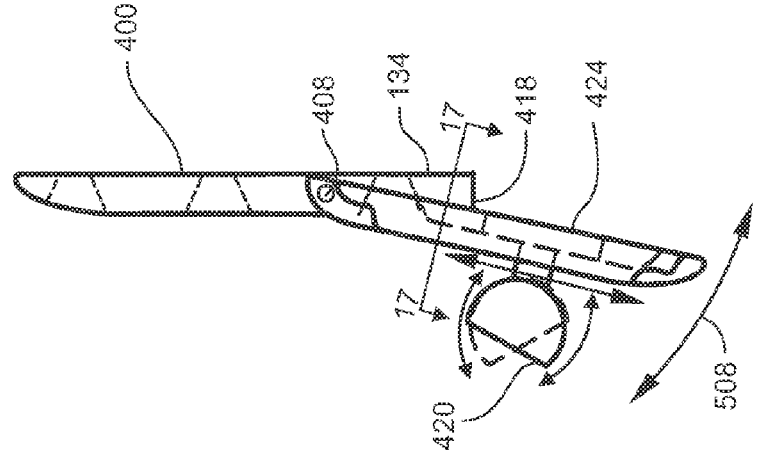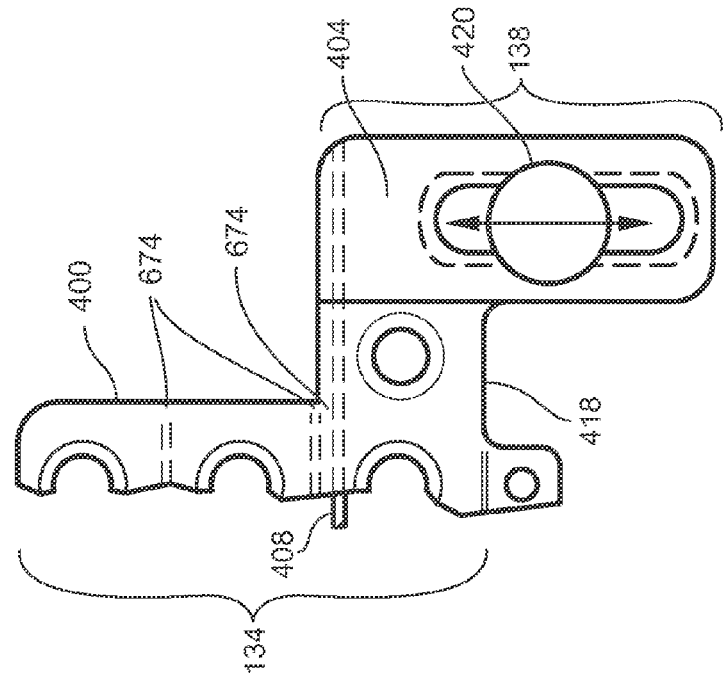

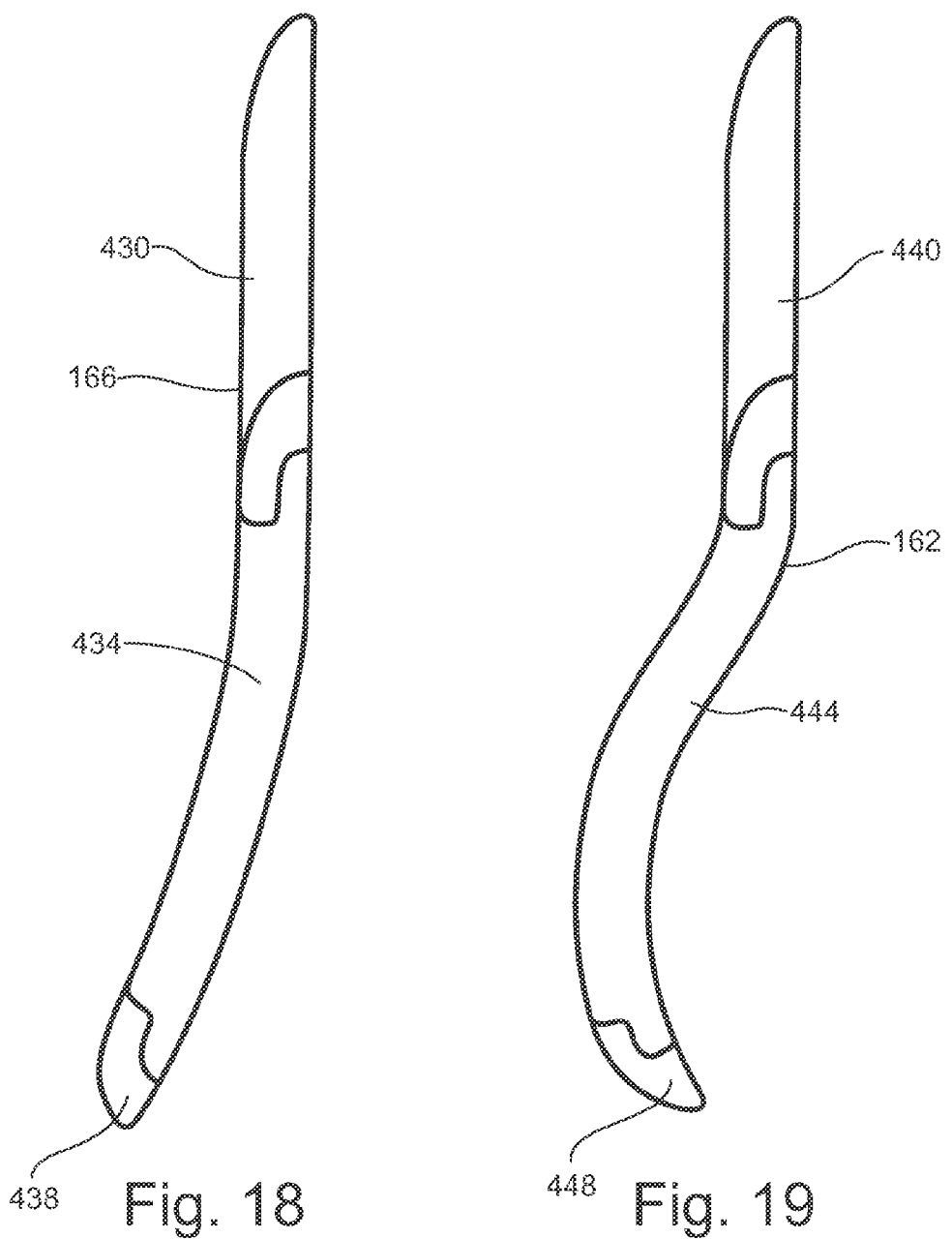

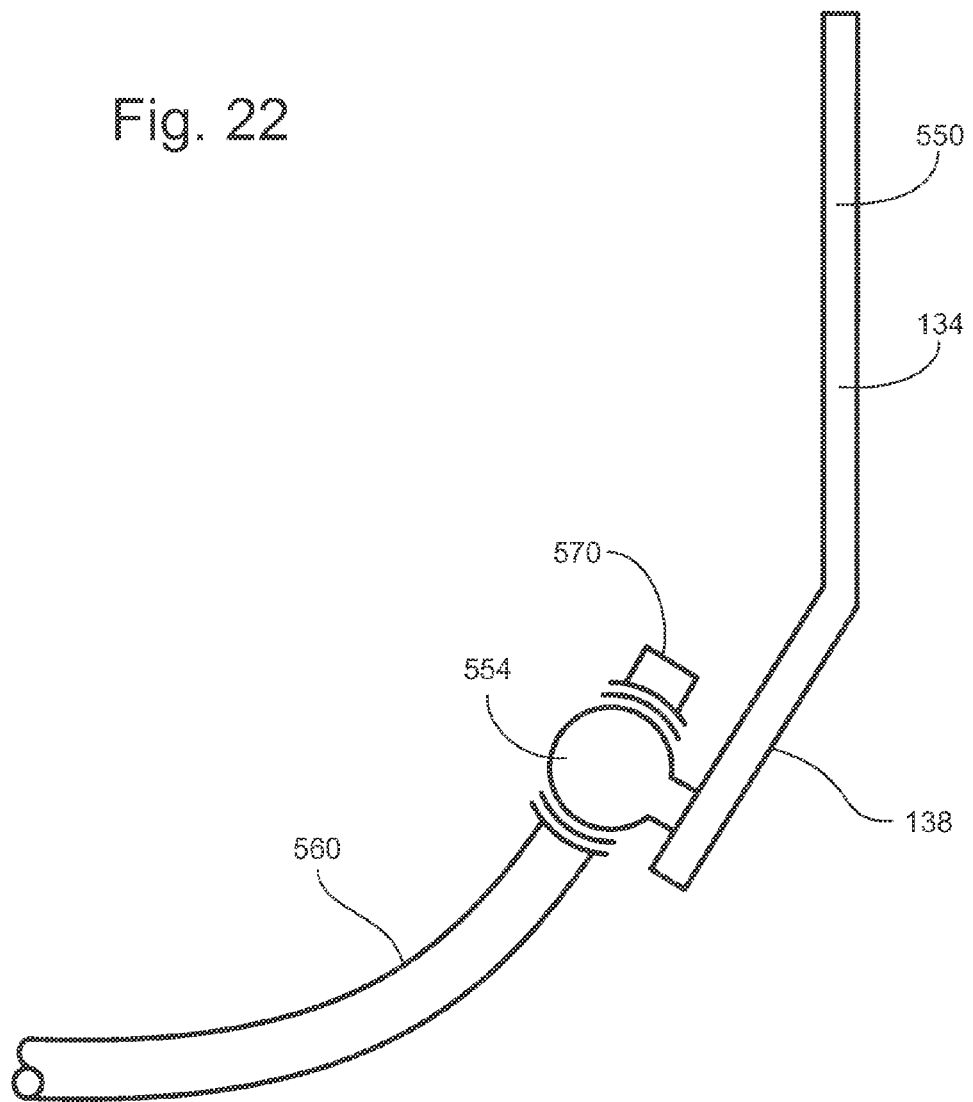

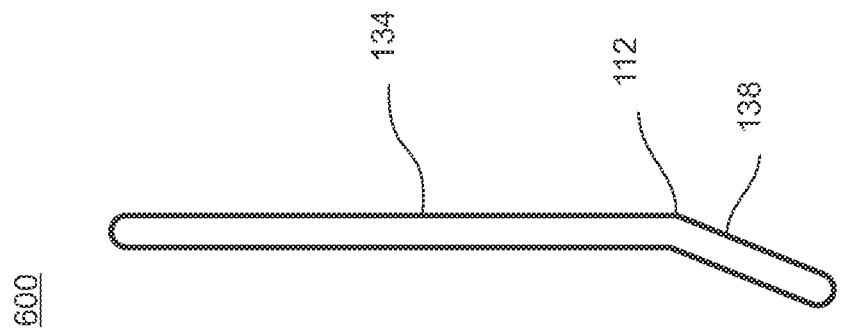
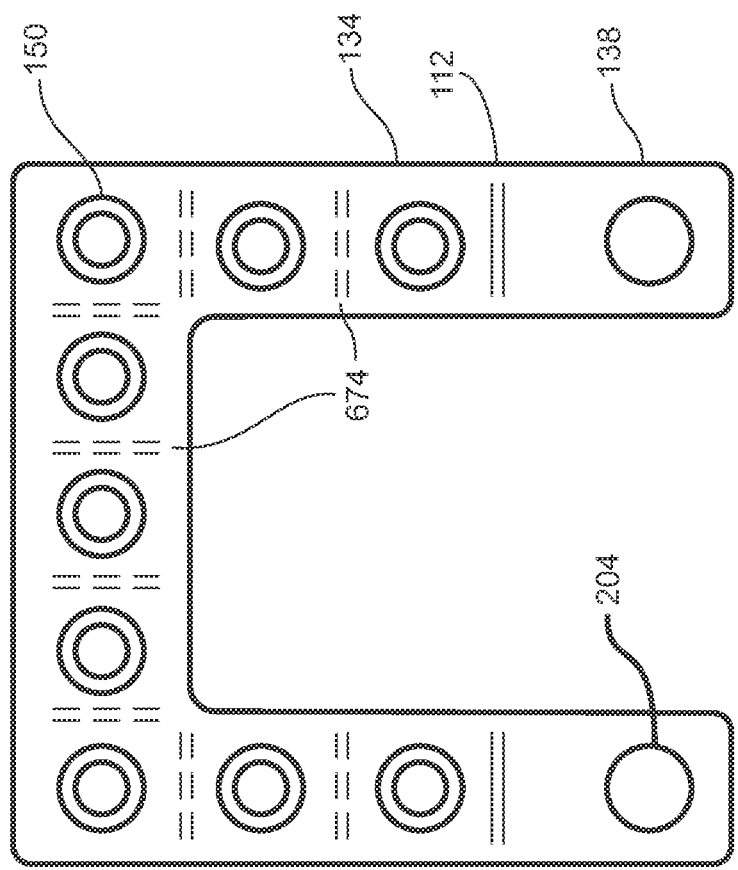

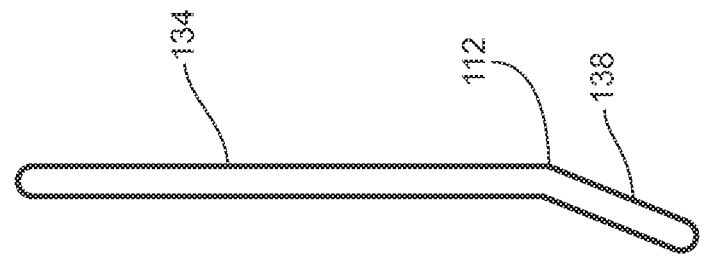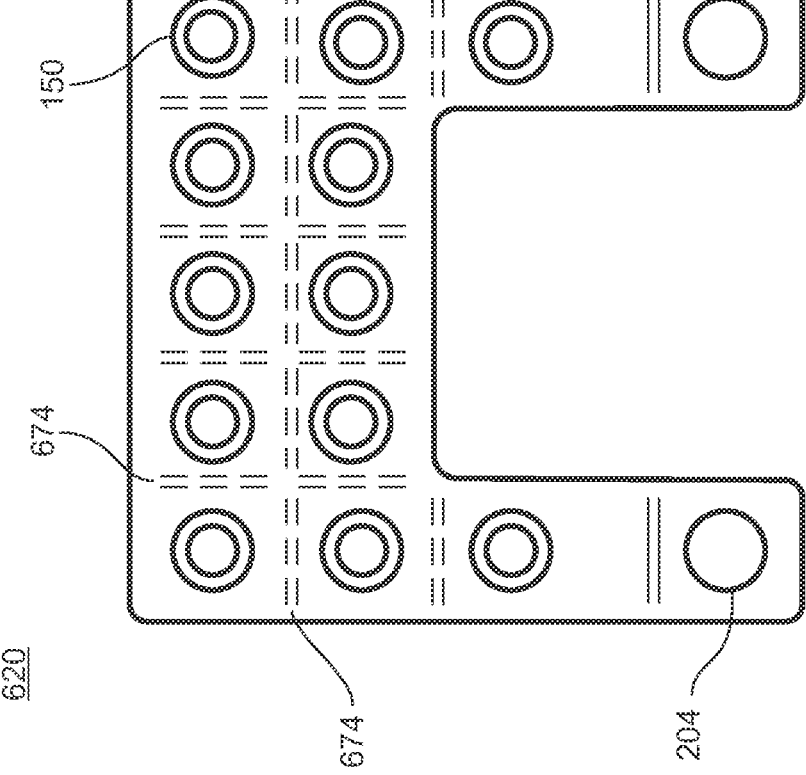

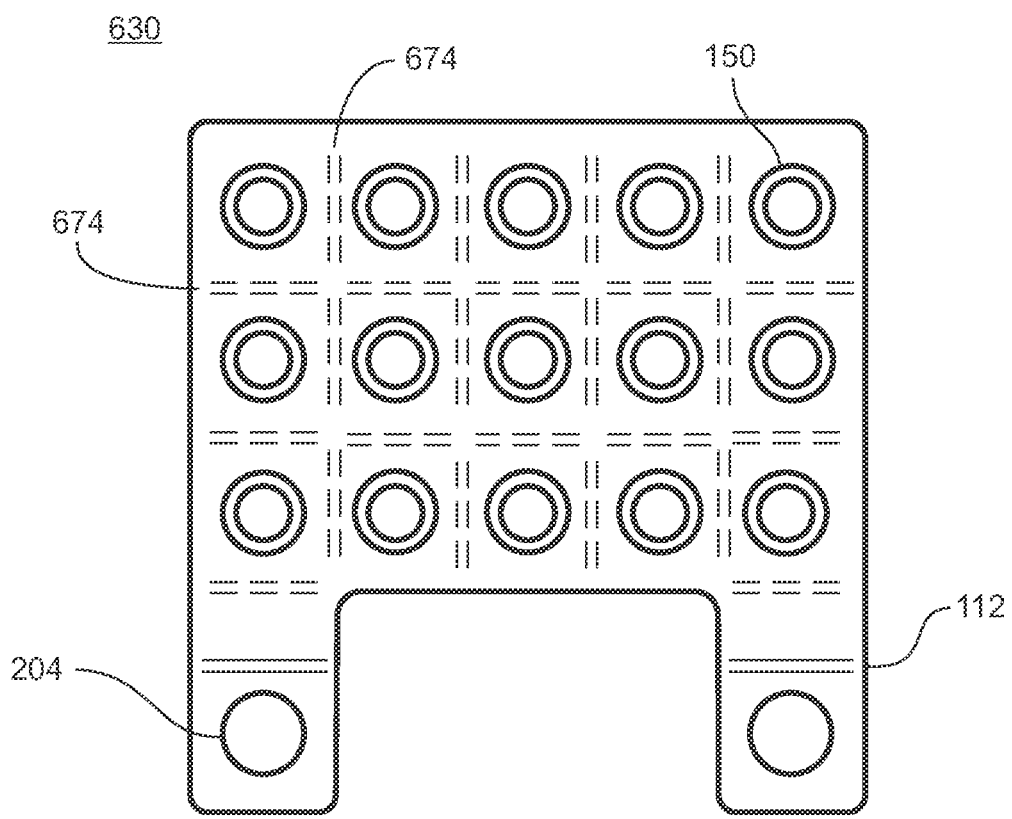

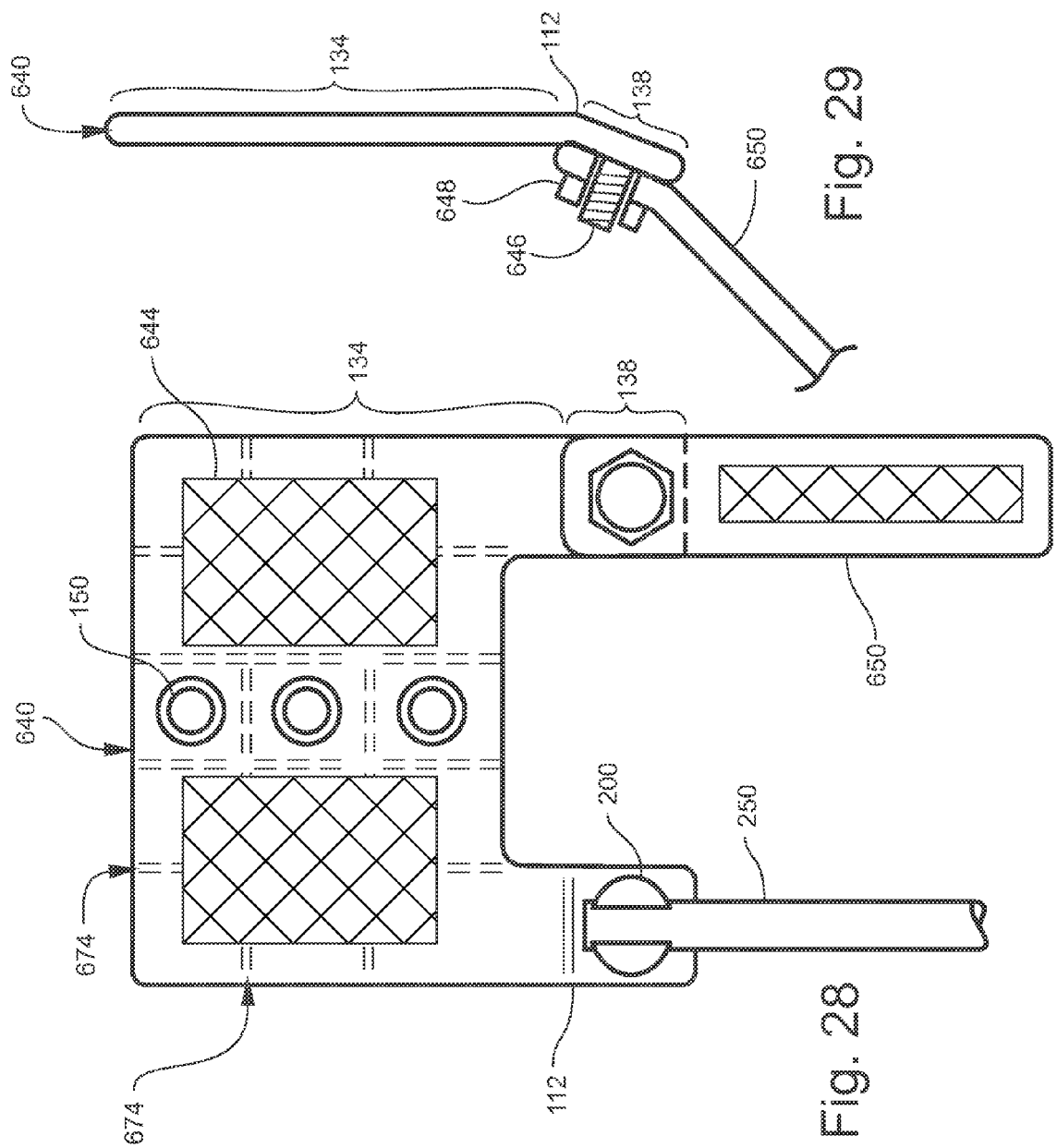

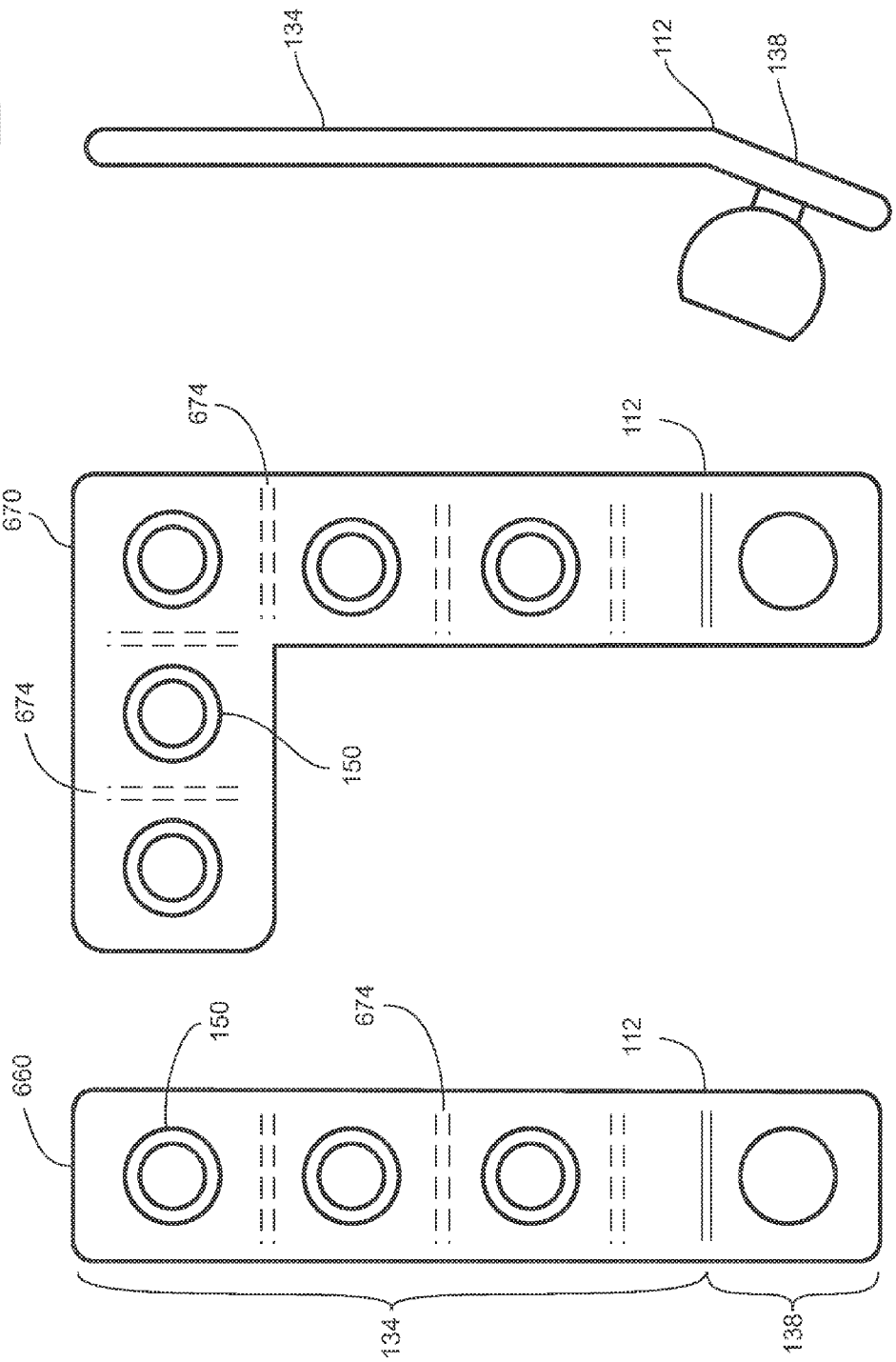

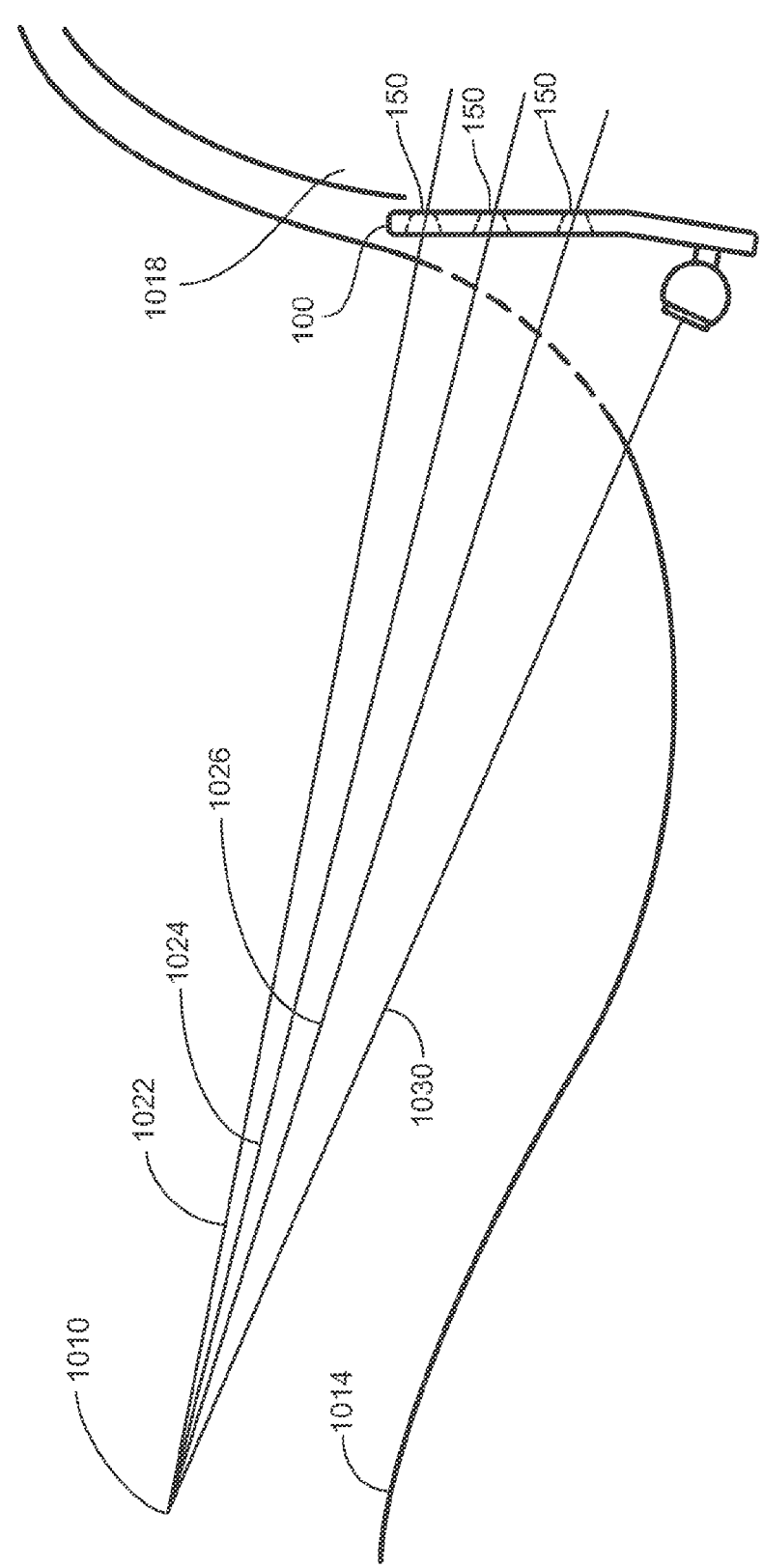

OCCIPITAL PLATE ASSEMBLIES WITH POLYAXIAL HEAD CONNECTORS

This application is a National Stage Entry of PCT/US2014/013682, which was filed on Jan. 29, 2014, and incorporates by reference and claims the benefit of U.S. Provisional Patent Application No. 61/849,553 filed Jan. 29, 2013 with title Occipital Spinal Implant System and Method.

FIELD OF THE DISCLOSURE

The present disclosure relates to spinal stabilization by mechanically fixing a region of a skull to a posterior portion of a spine. More particularly, this disclosure is directed to occipito-cervico-thoracic systems utilizing one or more plates attached to bone in the occipital (posterior) region of the skull and secured to a rod or plate which attaches to cables, wires, tapes, hooks, or screws fastened in the spinal region.

BACKGROUND

The reasons for surgical intervention for fuse the occipital cervical joints are varied, but the reasons can be categorized as falling within one of five fundamental categories.
 Neurologic Disorder;
 Mechanical Changes to the Spinal Column resulting in pain;
 Instability;
 Deformity; and
 Pathological Reasons-such as tumors or infection.

The skull may be viewed as a continuation of the spinal column. Sometimes surgical intervention is justified to fuse a series of one or more vertebrae in the spinal column. Likewise, there are situations that justify fusing the occipital portion of the skull to at least the C1 vertebra and often to the C2 vertebra or the C2 and C3 vertebrae. Some situations require fusing past the C3 vertebra possibly as far as the upper thoracic vertebrae.

Surgery is only justified when non-operative treatments are either ineffective or not an option. A non-exhaustive list of the specific reasons for surgical intervention that fall within these broad categories includes the following reasons. Instability of the occipitocervical joints may result from, for example, trauma (to the ligamentous structures of the craniocervical junction; fracture, or dislocation); degenerative disease processes (e.g., rheumatoid arthritis with vertical migration of the odontoid; degenerative spondylosis; spondylolisthesis; spinal stenosis); tumor; infection, or congenital malformation. Instability of the cervicocranium may lead to significant pathological translation, longitudinal displacement, or basilar invagination. Cervical cord compression and trauma to the spinal cord or the brainstem can result in respiratory distress, pain, cranial nerve dysfunction, paresis and paralysis, or even sudden death. Therefore, the need for occipitocervical stabilization may exist for patients with pathological instability.

Occipitocervical arthrodesis, or fusion, provides needed biomechanical stability and is a therapy used to treat such instability. Occipitocervical arthrodesis comprises decortication, deployment of appropriate spinal instrumentation and assemblies, and placement of structural and supplemental bone graft around the decorticated bony elements of the cranium and cervical vertebrae. In some instances the therapy may extend beyond the cervical spine to more caudal vertebral levels. The objective is to create a stable biomechanical environment and provide the biological requirements for osseous fusion. Adequate anterior spinal cord support for load sharing with the posterior implant construct is recommended. Adequate decompression of the neurological structures, where indicated, and recreation of normal sagittal and coronal alignment are prerequisites prior to an arthrodesis procedure. Due to the nature and location of this surgical procedure, adverse events can be serious and cause further neurological injury or impairment; vascular injury; cerebrospinal fluid (CSF) egress; infection; instrumentation failure; pseudoarthrosis; continued instability, deformity, and pain.

Occipitocervical fixation has been achieved using a variety of techniques to provide stabilization and/or alignment of the base of the skull with respect to the neck, followed by fusion, or arthrodesis by means of bone graft insertion. Existing surgical techniques and assemblies known in the art include posterior wiring/rods (for example, sublaminar and interspinous wires); screws/rods; hooks/rods; screws/plates; wires/plates, and posterior wiring with onlay graft.

Within these groups, there are various construct configurations, including hybrid systems. Initially, methods for achieving posterior occipitocervical stabilization included onlay fusion and simple wire techniques that required periods of traction followed by a halo, and rod and wire assemblies that were more stable, but continued to have difficulty preventing axial loads due to the rods pistoning through the sublaminar wires.

While occipito-cervical-thoracic stabilization procedures, and in particular posterior occipitocervical fusion surgical implants, instrumentation, and techniques, continue to evolve in the pursuit of improvements in clinical outcomes (e.g., the highest fusion rate with the shortest time to fusion and improvement in neurological function), and in simplicity of use, notwithstanding, there remains a need for ongoing advancements in plate, rod and screw assemblies leading to progress in the surgical management of complex cervical disorders, to accommodate an increased spectrum of anatomical variations, to enable simplicity of instrumentation placement, and to avoid certain adverse events such as loss of spinal alignment, in order to achieve more rigid stabilization in a wider variety of spinal diseases.

More particularly, plate and screw assemblies known in the art have multiple limitations, including fixed hole-to-hole or inter-rod distances that may not match patient anatomy and may prevent optimal occipital screw placement, compromising construct strength. These systems also have been known to experience failures (e.g., loosening, breakage, or cutout), including rod failure (breakage or telescoping), plate failure (fracture), or screw failure (breakage, migration or pullout). Moreover, in addition to the need to overcome problems of screw loosening, there exists a need for occipital plate systems for spinal stabilization in which the occipital plate:
 does not obscure the surgeon's view as a screw is being inserted,
 has a profile that maximizes space for graft material;
 can support compression or distraction between the anchored occipital plate and other anchored components; and.
 is configured to permit greater flexibility in deployment with the rods by the surgeon to achieve optimum fit.

There are disclosed herein surgical implants, instruments and methods for occipitocervical fusion which allow independent insertion of the screw anchors as well as stable connection to the longitudinal rod, and permit greater flexibility and adjustability during surgery via a universal, polyaxial connection means for securing an occipital plate to a spinal rod or plate. It is believed that the use of the systems disclosed herein will overcome limitations noted above and that will result in improved maintenance of alignment, increased rate of successful arthrodesis, and minimized occurrence of adverse events as evidenced by clinical and radiographic outcomes.

General Comments and Terminology.

In the context of the present disclosure, as used herein the terms "assembly" or "assemblies" are sometimes used interchangeably and refer to implants, implant systems, instruments, or instruments systems which are configured to comprise multiple components, which may or may not be contiguous. It is further understood that individual components may themselves be configured as sub-assemblies, e.g., comprising a plurality of component materials, and that the formation of the components may involve intermediate processes or appliances.

It will also be understood that upon formation of assemblies from multiple components and deployment, individual components of the present disclosure may or may not remain as discernibly distinct. It will also be understood that, for convenience, system components may be packaged and provided either individually, or as in "kits," and either as reusable or disposable.

It will be further understood that the length and dimensions of implant components and instruments described herein will depend in part on the target site selection of the treatment procedure and the physical characteristics of the patient, as well as the construction materials and intended functionality, as will be apparent to those of skill in the art.

In order to make it easier for a reader to find certain sections of this document that are of particular interest to the reader, a series of headings have been used. These headings are solely for the purpose of helping readers navigate the document and do not serve to limit the relevance of any particular section exclusively to the topic listed in the heading.

The sequence of operations (or steps) is not limited to the order presented in the claims or figures unless specifically indicated otherwise.

It will also be understood that as used herein, rod supporting portion of the occipital plate may also refer to, for example, a plate supporting potion, that is, the area of the occipital plate which is configured and adapted to engage a connection assembly that connects the occipital plate to the spinal portion of the skull-vertebral construct.

It will also be understood that as used herein, the terms rod, spinal rod, longitudinal rod, or plate (e.g., cervical) are sometimes used interchangeably and refer to devices within the stabilization construct that connect and align the occipital plate and skull with the cervical (or thoracic) vertebrae.

SUMMARY OF THE DISCLOSURE

Occipitocervical posterior fixation devices generally include an occipital plate fastened to the posterior portion of the skull, or occiput; one or more spinal rods or plates running longitudinally along the spine and connected to the occipital plate, and other connectors (e.g., other plates, cables, wires, tapes, hooks, screws) attached to a vertebra and connected to the longitudinal rod or plate. One aspect of the present disclosure is related to an occipital plate that includes a flexible configuration for the occipital plate connection to the spinal rod.

An occipitocervical fixation system is disclosed that comprises an occipital plate for securing to the occiput of the skull and at least component to link the occipital plate to another assembly that is connected to the spine. For example one or more spinal rods may connect to the occipital plate through a polyaxial connector assembly. These spinal rods are connected to other components that are anchored to the spine. Alternatively, the occipital plate may be connected to a cervical plate.

The polyaxial connector assembly may include a ball joint to allow 360 degree rotation of the polyaxial connector assembly. The poly axial connector assembly may include a collet to allow the polyaxial connector assembly to reversibly lock a position of the polyaxial connector assembly relative to the another assembly that is connected to the spine.

As described in detail below, the polyaxial connector section may experience movement while in a first constrained mode constrained by an elongated slot in the connector section, the movement being a mix of movement along the cephalad/caudal axis and the anterior/posterior axis, and each polyaxial connector section may be placed in a second locked mode wherein the polyaxial connector section may no longer experience movement constrained by the elongated slot. (See FIG. 1 below for explanation of the relevant axes.)

The occipital plate may have an occipital bony attachment section with an array of through holes for securing the occipital plate to a portion of the skull. The through holes allow a bone screw to pass from the posterior side of the occipital plate through to the anterior side of the occipital plate and into portions of the skull. The bone screw may be a bicortical screw.

The occipital bony attachment section may include at least one mesh portion for receipt of bone screws to allow a distal end of the bone screw to pass through the mesh portion and enter the skull while capturing a proximal end of the bone screw so that the bone screw pulls the mesh portion towards the skull.

As described below, the occipital plate and the through holes may be adapted to allow the delivery of bone screws with straight instruments through compensation for the thoracic hump. For example, the through holes may be angled, so that they are not perpendicular to the occipital bony attachment section of the occipital plate, to overcome certain anatomical issues such as the thoracic hump while allowing the use of straight drills, taps, drivers, and extraction tools.

The occipital plate may have at least one connector section, caudal to an inflection zone that separates the occipital bony attachment section from the connector section, the connector section offset posterior from an extension of the occipital bony attachment section. The connection section may be offset in a posterior direction from an extension of the occipital bony attachment section via a fixed angle at the inflection zone. The connection section may be offset in a posterior direction from an extension of the occipital bony attachment section via a lockable hinge. The connection section may be offset in a posterior direction from an extension of the occipital bony attachment section via a curved connection section. The curve can be concave with respect to the posterior side of the occipital plate or concave with respect to an anterior side of the occipital plate.

The occipital plate may include at least one cable connector section which may have a through hole for connecting a cable, wire, or tape to the cable connector section.

Given that the occipital plates allow for a range of adjustment to adjust for patient anatomy, including the polyaxial connection between the occipital plate and another assembly connected to the spine, suitable fits may be achieved with a limited number of different occipital plates. This is an advantage in that the need for multiple sizes causes a need to maintain a higher overall inventory of occipital plates in order to have a number of occipital plates in each of the available sizes. If the primary method of getting a plate to conform to the geometry of a patient is to select a particular occipital plate from a series of choices, then the surgeon must spend time measuring various aspects of patient geometry and possibly trying two or more possible candidates for fit.

In contrast, a system with a fewer number of highly adjustable plates (perhaps, infant, juvenile, small adult, and large adult) would allow the surgeon to quickly select an appropriate occipital plate and then adjust the occipital plate to the patient through intraoperative adjustments.

Additionally, the disclosed occipital plate angled tab configuration for rod connection accommodates a wide variety of available polyaxial connectors; the angled tab enables improved line of sight in assembling and deploying the construct; enables the use of straight, i.e., non-angled, or non-articulating instruments, and increases the ability to deploy increased bone graft volume. Bone graft material may be placed between the angled connector sections and may be placed behind the angled connector sections and the one or more cable connector sections as these sections are angled in a posterior direction.

In another aspect of the present disclosure, an occipital plate and optionally one or more spinal rods may be segmented and bendable for optimum fit to accommodate the needs of individual patient anatomy. For example, the occipital plate may be configured to comprise elements, such as lines of reduced plate thickness, notches, or cut-outs that facilitate contouring.

The lower profile, tapered edge occipital plates disclosed herein have additional advantages when compared with prior art systems, including improved pull-out strengths afforded by a design which maximizes placement of bone fastener holes and is compatible with the use of a variety of bone fastener elements other than screws, such as for example, expansion bolts.

In yet another aspect of the present disclosure, the unthreaded holes allow the screws which are disposed therein to articulate with the plate and preclude gaps between the occipital plate and the skull. It is preferable to position holes along the central portion of the plate for use at the midline of the occiput, where bone thickness is greatest. It is also desirable to have multiple holes for screws to maximize pullout strength and stability.

Thus, in one aspect of the present disclosure, the occipital plate spinal stabilization systems are configured to maximize the ability to place occipital screws along the midline, the thickest and strongest area of bone in the occiput, and wherein bicortical occipital screw placement in the thickest and strongest bone along the occipital midline offers a biomechanical advantage and promotes stability, thereby increasing fusion rates.

Screws are the most common type of bone fastener attachment of the occipital plate to skull. While the use of bicortical screws is preferred for better pullout strength, use of unicortical screws may be acceptable. Additionally, although the option exists for use of locking screws, non-locking screws are more commonly used. The use of parallel screws is acceptable, but in yet another aspect of the disclosure, the occipital plate described herein may be configured to accept angled screws to facilitate the use of direct coaxial drill, tap, and driver. Divergent/convergent screws increase the pullout strength of the plate as compared to parallel screws. In other examples, the use of alternative fasteners, e.g., expansion bolts; and the like, is also acceptable.

One way of summarizing various teachings of the present disclosure is:
An occipital plate assembly for use in a therapeutic procedure, the occipital plate assembly comprising:
an occipital plate comprising:
an occipital bony attachment section with an array of through holes for securing the occipital plate to a portion of a skull;
at least one connector section, caudal to an inflection zone that separates the occipital bony attachment section from the connector section, the connector section offset posterior from an extension of the occipital bony attachment section; and
each connector section having at least one polyaxial connector assembly to connect the occipital plate to another assembly for connection with a spine, the polyaxial connector assembly having a capacity to move along a cephalad/caudal axis and laterally in order to align an opening in the polyaxial connector assembly with a portion of the another assembly.

Another way to summarize various teachings of the present disclosure is:
An occipital plate assembly for use in a therapeutic procedure, the occipital plate assembly comprising:
An occipital plate comprising:
an occipital bony attachment section with an array of through holes for securing the occipital plate to a portion of a skull;
at least one connector section, caudal to an inflection zone that separates the occipital bony attachment section from the connector section, the connector section offset posterior from an extension of the occipital bony attachment section; and
each connector section having at least one threaded element to connect the occipital plate to a cervical plate for connection with a spine.

A third way to summarize various teachings of the present disclosure is:
A cervical plate for use in a therapeutic procedure, the cervical plate comprising:
at least one mesh portion for receipt of bone screws to allow a distal end of the bone screw to pass through the mesh portion and enter a portion of a spine while capturing a proximal end of the bone screw so that the bone screw pulls the mesh portion towards the portion of the spine; and
an opening near a cephalad end of the cervical plate to allow a threaded shaft from an occipital plate to pass through the opening so that a nut can secure the cervical plate to the occipital plate.

A fourth way to summarize various teachings of the present disclosure is:
A method for affixing an occipital plate to an occipital region of a skull, the method comprising:
placing an occipital plate assembly adjacent the occipital region of the skull, the occipital plate assembly comprising:
an occipital bony attachment section with an array of through holes for securing the occipital plate to a portion of a skull wherein the through holes have openings on a posterior side of the occipital plate that are larger than openings on an anterior side of the plate and the through holes have centerlines offset from perpendicular to the occipital bony attachment section to compensate for a thoracic hump and allow straight bone screw drivers;

at least one connector section, caudal to an inflection zone that separates the occipital bony attachment section from the connector section, the connector section offset posterior from an extension of the occipital bony attachment section; and each connector section having at least one polyaxial connector assembly to connect the occipital plate to another assembly for connection with a spine, the polyaxial connector assembly having a capacity to move along a cephalad/caudal axis and laterally in order to align an opening in the polyaxial connector assembly with a portion of the another assembly;

using a straight bone screw driver, secure the occipital bony attachment section of the occipital plate assembly to the occipital region of the skull;

engage the at least one polyaxial connector assemblies with a spinal rod connected to a component anchored in a spine; and lock the at least one polyaxial connector assemblies to preclude subsequent movement of the spinal rod with respect to the locked polyaxial connector assembly.

Aspects of the teachings contained within this disclosure are addressed in subsequent claims submitted with this application. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The accompanying figures, which are incorporated in and constitute part of this specification, are included to illustrate and provide a further understanding of the system and method of the disclosure. Together with the description, the figures serve to explain the principles of the disclosure. Unless indicated, the components in the figures are not necessarily to scale, emphasis instead being placed upon illustrating the principles of the disclosure. Moreover, in the figures, like referenced features designate corresponding parts throughout the different views.

FIG. 4 illustrates a variety of locations for cable connection through holes 148 in alternative occipital plate 180.

FIG. 7 shows a polyaxial connector assembly rotated in the medial direction.

FIG. 8 shows a polyaxial connector assembly rotated in the lateral direction.

FIG. 9 shows occipital plate 100 with a pair of polyaxial connector assemblies 200 rotated to both engage the same unitary spinal rod 252 and the option of having a pair of L-shaped rods.

FIG. 10 provides a side view of the assembly shown in FIG. 9.

FIG. 12 shows the anterior side of an occipital plate with a welded connection to a polyaxial connector assembly.

FIG. 13 shows a posterior view of an occipital plate with elongated slots for use with the polyaxial connector assembly.

FIG. 14 shows a side view of the occipital plate from FIG. 13.

FIG. 15 shows a posterior view of a portion of an occipital plate with an elongated slot.

FIG. 16 shows a side view of the occipital plate from FIG. 15.

FIG. 17 shows a cross section of a portion of FIG. 16

FIG. 18 shows a side view of an occipital plate with a curved connector section that is concave to the posterior face.

FIG. 19 shows a side view of an occipital plate with a curved connector section that is concave to the anterior face.

FIG. 22 shows a side view of an occipital plate connected to a cervical plate via a snap on connector.

FIG. 23 shows a posterior view of an occipital plate adapted for use after a suboccipital craniectomy or when a maximized array of screws is needed for use with a weak occipital bone.

FIG. 24 shows a side view of the occipital plate from FIG. 23.

FIG. 25 shows a posterior view of an occipital plate adapted for use when the maximum number of screws is needed for weak occipital bone.

FIG. 26 shows a side view of the occipital plate from FIG. 25.

FIG. 27 shows occipital plate 630 with an even larger array of through holes 150.

FIG. 28 shows a posterior view of an occipital plate with a mesh portion in the occipital bony attachment section and a cervical plate 650 with a mesh portion.

FIG. 29 shows a side view of the occipital plate from FIG. 28.

FIG. 30 shows a posterior view of a pair of occipital plates adapted for use after a suboccipital craniectomy or in other instances where a unilateral plate is needed.

FIG. 31 shows a side view of an occipital plate from FIG. 19.

FIG. 32 illustrates an array of insertion paths from a common point 1010 which is comfortably above the thoracic hump 1014.

DETAILED DESCRIPTION

The present application has a range of teachings that may be used to advantage in a number of settings. However, to provide these teachings with clarity, it is useful to describe one use of many of the teachings in detail. Those of skill in the art are familiar with various surgical techniques for achieving occipitocervical fusion. As this is not the focus of the present application, those processes are not included in detail here. Rather, the present disclosure sets forth examples of occipital plates illustrating, for example (but not limited to), an advantageous occipital plate-rod connection configuration that permits polyaxial angulation of the spinal rod relative to the occipital plate and enables the method of use of the system as disclosed.

Figure 1:
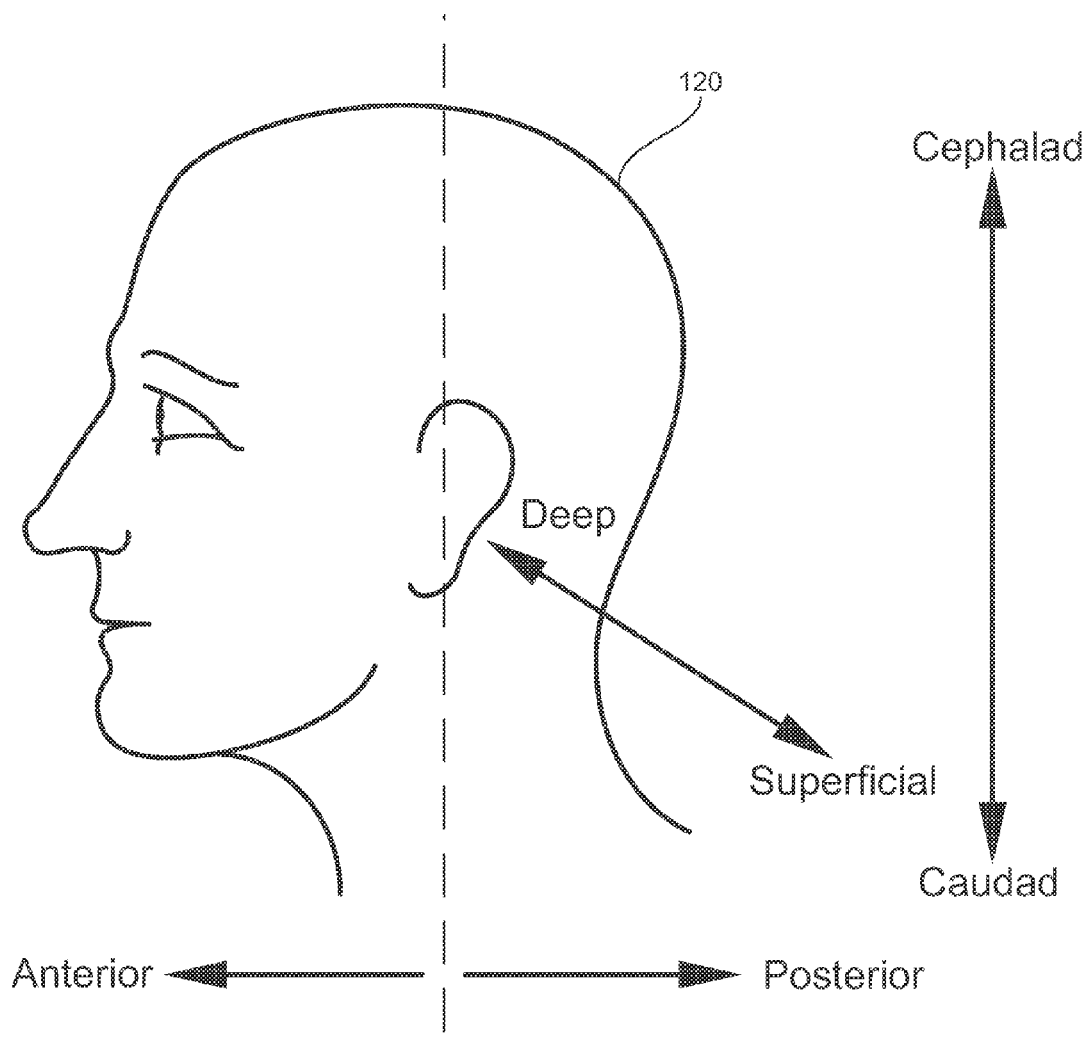
FIG. 1 introduces the coordinate axes for the discussion that follows.

FIG. 1 introduces the coordinate axes for the discussion that follows with a lateral view of a head with skull. As shown in FIG. 1 anterior refers to the front side of the patient and posterior refers to the back side of the patient. With respect to components placed on the posterior side of the patient, the anterior side would be the side facing the posterior of the patient and the posterior side would be the side facing away from the patient. Cephalad means towards the patient's head; caudal refers to the direction or location that is closer to the feet.

Other terms indicating direction not shown in FIG. 1 include: medial, lateral, distal, and proximal. When looking at the posterior view of the patient, medial indicates situated on the median plane of the patient, and lateral is away from the median plane. Proximal is closer to the surgeon; distal is in use more distant from the surgeon. When referencing tools, distal would be the end intended for insertion into the patient and proximal refers to the other end, generally the end closer to the user such as a handle.

Figure 3:
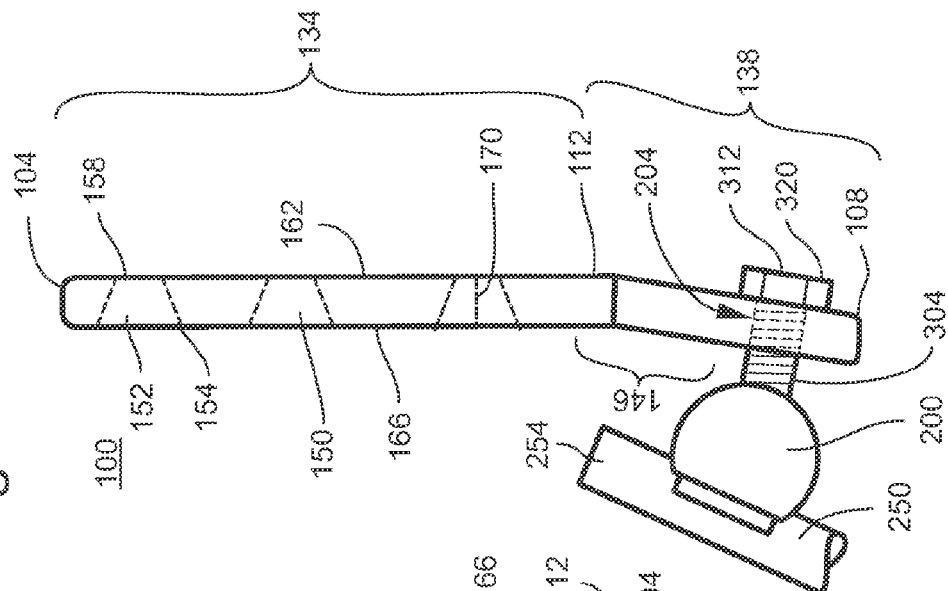
FIG. 3 provides a side view of occipital plate 100.
Figure 2:
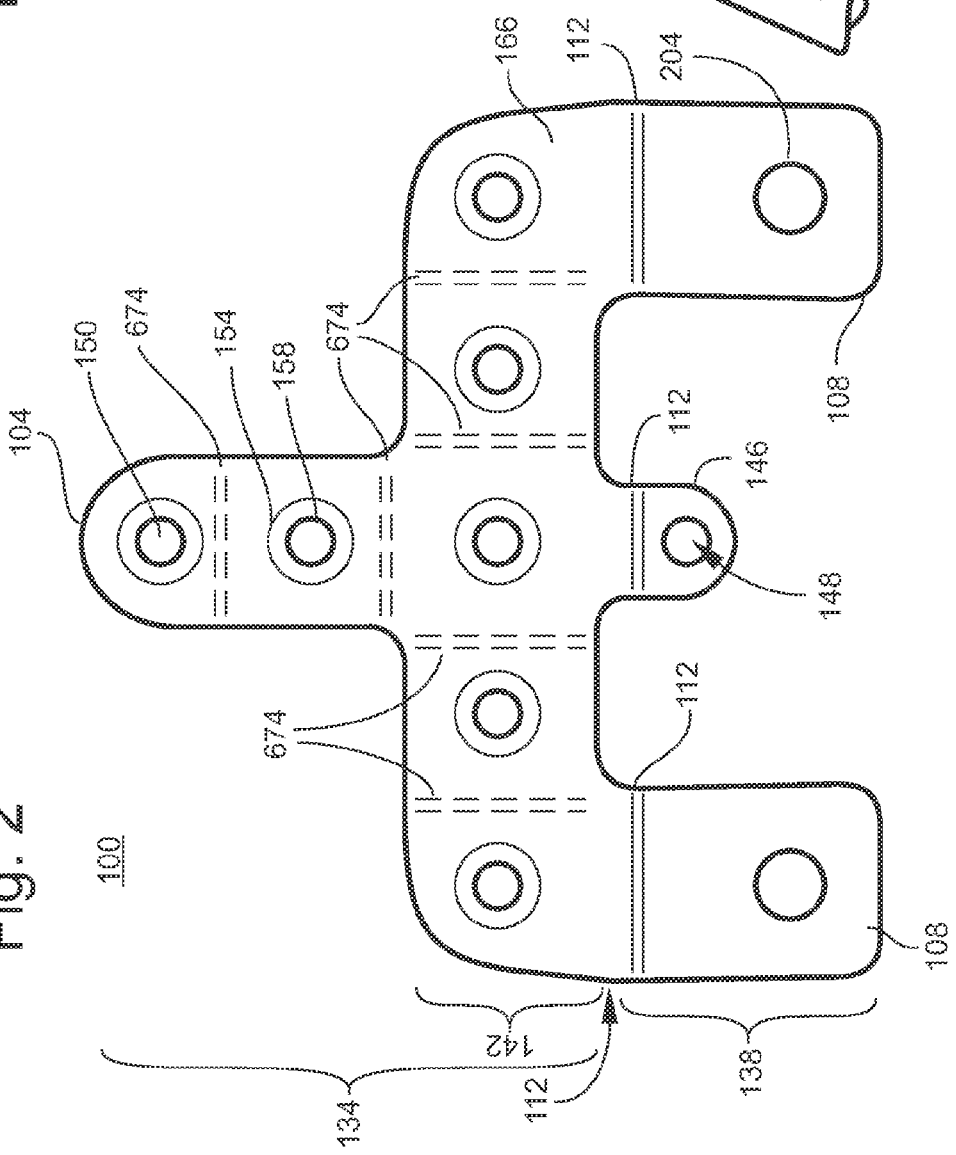
FIG. 2 provides a posterior view of an occipital plate 100.

FIG. 2 is a posterior view of occipital plate 100. FIG. 3 is a side view of the same occipital plate 100 with a connected polyaxial connector assembly 200 and a portion of a spinal rod 250. The occipital plate 100 has a cephalad end 104 and a caudal end 108. As seen in FIG. 3, an inflection zone 112 separates a occipital bony attachment section 134 occipital bony attachment section 134 and an angled connector section 138 which is angled outward from an extension of the longitudinal axis of the cephalad section 124. The outward angle may vary from about sixty degrees to almost zero degrees.

Bone graft material to assist in fusing the skull to at least the C1 vertebra may be placed between the angled connector sections 138 and posterior to the angled connector sections 138.

The shape of the occipital plate 100 may have occipital bony attachment section 134, a pair of angled connector sections 138, and a crossbar section 142 between the occipital bony attachment section 134 occipital bony attachment section 134 and the pair of angled connector sections 138. Optionally, a cable connector section 146 may be connected to the crossbar section 142, caudal to the occipital bony attachment section 134 occipital bony attachment section 134 and between the pair of angled connector sections 138.

The cable connector section 134 has a cable connection through hole 148. The occipital bony attachment section 134 occipital bony attachment section 134 of the occipital plate 100 may be sized to be secured along the midline of the occiput or skull.

Those of skill in the art will recognize that the various cable connector sections 146 shown in the drawing sets are essentially plates. Thus, the cable through holes 148 are shown passing through the plates from the posterior side of the cable connector section 146 to the anterior side of the cable connector section 146. The teachings of this disclosure are not limited to that specific geometry. For example, the cable connection section could be in the form of a cylinder, thick plate, or other shape such that the cable through holes may oriented laterally.

FIG. 4 illustrates a variety of locations for cable connection through holes 148 in alternative occipital plate 180. In addition to cable connector section 146, occipital plate 180 has a pair of cable connector sections 144 which are extensions of the angled connector section 138. Additional cable connection through holes 148 may be placed near the caudal end of the angled connector section 138. One of skill in the art will recognize that the cable connector section 146 may be omitted from an occipital plate if alternative placements for cable connection through holes are provided.

Those of skill in the art will recognize that the cable through holes 148 while shown as round in the various drawings in this disclosure could be other shapes. The cable through holes could be slots or other shapes to work with the termination hardware on the relevant cable or other analogous tension device.

The occipital plate 100 may have a plurality of through holes 150. These through holes 150 may be unthreaded with the posterior openings 154 (facing away from the skull) significantly larger than the anterior openings 158 (facing the skull). While one could adapt the teachings of the present disclosure with threaded through holes, the use of unthreaded through holes allows the bone screws (not shown) to act like lag screws to pull the occipital plate to the skull. One example of a bone screw for illustration purposes is a bone screw with a 6 millimeter head and an outer diameter of 3.5 to 4.5 millimeters. The screws may come in a variety of lengths in the range of 10 millimeters to 26 millimeters. The use of locking screws is another option.

The occipital plate 100 in FIG. 2 shows a two dimensional array of seven through holes 150. The teachings of the present disclosure do not require specifically seven through holes 150 and allow for other patterns of distribution of through holes 150. Having a relatively large number of through holes 150 allows a corresponding number of bone screws to be used. As a general rule, increasing the number of bone screws increases the pull out strength for pulling the occipital plate 100 from the skull.

The interior 152 of the through holes 150 may be bowl shaped with curved sides rather than angled sides. By using the same radius of curvature as the screw heads, the curved sides provide more contact area between the screw head and the walls of the through holes 150. The interior shape of the through holes also facilitates placing the bone screws at an angle relative to the occipital plate 100.

As seen in FIG. 3, the centerline 170 of through hole 150 may be oriented perpendicular to the anterior side 162 of the occipital plate 100. Optionally, the centerline 170 may be altered to have as much a 60 degree offset from perpendicular. The offset would place the posterior opening 154 slightly offset above the anterior opening 158. This angle offset may allow use of instruments for driving the bone screws that are straight. The use of through holes 150 with centerlines 170 set perpendicular to the anterior side 162 of the occipital plate 100 may require bone screw drivers that compensate for the thoracic hump. One option is to use more pronounced angle offsets for one or more the most caudal through holes 150 and progressively less pronounced angle offsets for more cephalad through holes 150. The angle offsets help not only with bone screw drivers but also with the earlier steps of drilling and tapping if tapped. An additional advantage of the angled offsets is that by using different angled offsets for different through holes 150, the pullout strength of the connection of the occipital plate 100 to the skull is increased.

Optionally, the anterior side 162 of the occipital plate 100 may have one or more anti-migration features to reduce the tendency of the occipital plate 100 to move relative the skull once place in contact with the skull. The anti-migration feature may be spikes or other protrusions. The anti-migration feature may be a surface treatment to increase surface friction such as may be achieved by bead blasting. Anti-migration features may be dimensioned and configured so as not to cause damage to surrounding or underlying soft tissue and so as not to preclude the ability of an occipital plate 100 to conform and fit to the skull without gaps. The posterior side 166 of the occipital plate 100 does not require anti-migration features. Thus, a process such as bead blasting may be selectively applied to only the anterior side of the occipital plate 100 as that is the side that is in contact with the skull.

The anterior side 162 of the occipital plate 100 may be treated so as to promote bone ingrowth.

Angled Connector Sections.

Having a pair of angled connector sections 138 which bend away from the skull below the inflection zone 112 provides a location to affix a pair of polyaxial connector assemblies 200. These polyaxial connector assemblies 200 may be attached to connector through holes 204.

The polyaxial connector assembly 200 is configured to permit the surgeon to achieve desired polyaxial angulation or placement of the cephalad ends 254 of the spinal rod 250 relative to the occipital plate 100, prior to mechanically securing or locking the spinal rod 250 engaged to the polyaxial connector assembly 200 which locks in the relative position of the components comprised in the occipital plate 100 and spinal rods 250 construct.

The polyaxial connector assembly 200 may be configured to receive and engage spinal rods 250 with various diameters such as 3.5 millimeters, 4.5 millimeters, or other diameters based on the needs of the therapy.

The sequence of deployment may be to first attach the occipital plate 100 to a skull using a set of bone screws and then adjust each polyaxial connector assembly 200 to receive a portion of a spinal rod 250 near the cephalad end 254 of the spinal rod 250. Having polyaxial connector assemblies 200 facilitates this process.

Sample Polyaxial Connector Assembly.

Figure 5:
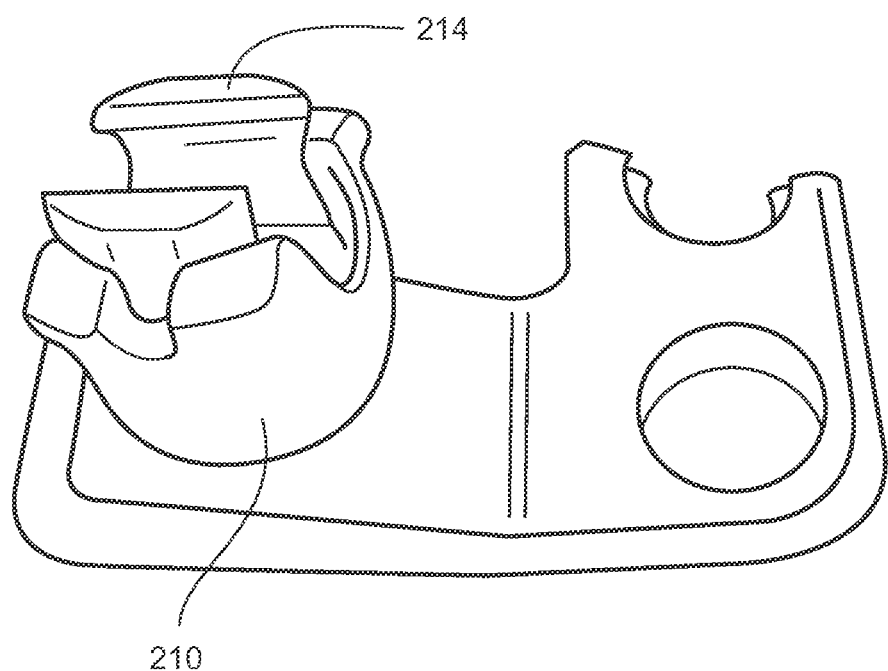
FIG. 5 shows a polyaxial connector assembly rotated in the caudal direction.
Figure 6:
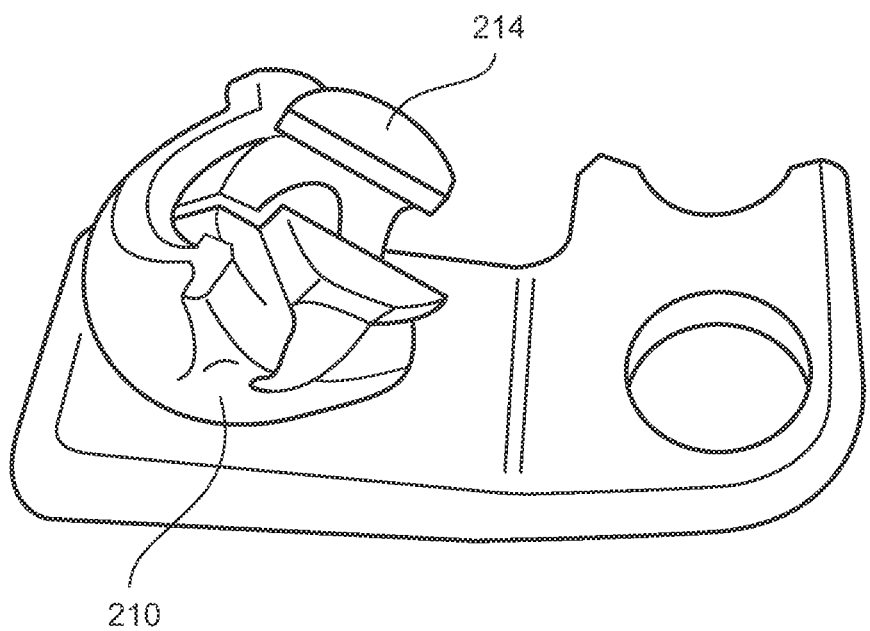
FIG. 6 shows a polyaxial connector assembly rotated in the cephalad direction.

FIG. 5 shows a polyaxial connector assembly 200 rotated in the caudal direction and FIG. 6 shows the same polyaxial connector assembly 200 rotated in the cephalad direction. This rotation happens through the movement of the external collet 210 and internal split collet 214 relative to an internal ball joint (not visible). The ball joint also allows the polyaxial connector assembly to rotate on the medial/lateral axis and combinations of the caudal/cephalad and medial/lateral. FIG. 7 shows the polyaxial connector assembly 200 rotated to the medial direction. FIG. 8 shows the same polyaxial connector assembly 200 rotated to the lateral direction.

Further, the ball joint allows the polyaxial connector assembly 200 to rotate around the connection to the occipital plate 100. The sum of these various allowable motions provides an ability to align the opening in the internal split collet 214 to be aligned with the spinal rod 250 including as discussed below, a spinal rod 250 that runs horizontally between the two polyaxial connector assemblies 200 in an alternative configuration.

Once the spinal rod 250 is seated in the internal split collet 214, lifting the external collet 210 (moving it posteriorly) causes the internal split collet 214 to clamp the spinal rod 250. Locking the position of the external collet 210 relative to the internal split collet 214, locks the spinal rod 250 to the polyaxial connector assembly 200. The locking can be achieved by a set screw, accessory screw, or other locking mechanism known to those of skill in the art. The locking mechanism can use an accessory screw, clip, crimp, spring, or the like Those of skill in the art with recognize that the polyaxial connector assembly with the internal split collet and external collet is a polyaxial connector marketed as part of the K2M® Mesa® System sold by K2M, Inc. This particular polyaxial connector assembly is provided as an example to explain the use of the various occipital plates disclosed in this application. Other polyaxial connectors may be used while still enjoying the advantages of the occipital plates disclosed in this application.

Use of Unitary Spinal Rod.

FIG. 9 shows occipital plate 100 with a pair of polyaxial connector assemblies 200 rotated to both engage the same unitary spinal rod 252. The unitary spinal rod 252 serves a dual purpose to serve as a stabilizing cross member and as a spinal rod connecting the occipital plate 100 to other components anchored to more caudal portions of the spine. FIG. 10 provides a side view of the assembly shown in FIG. 9.

An alternative implementation of the concepts in FIG. 9 could be implemented by reducing the medial/lateral width of the occipital plate 100 so that the occipital plate 100 could work with a range of unitary spinal rods 252 having different inter-rod widths 268 between cephalad/caudal portions 262 and 264. By allowing one occipital plate 100 that may receive a number of different unitary rods 252 with different inter-rod widths 268, the number of different occipital plates 100 to be stocked to accommodate different patient anatomies will be greatly reduced.

If instead of unitary rod 252, the assembly was made of L-shaped rod 272 which terminates at 256 after a right turn, and L-shaped rod 274 which terminates at 258 after a left turn, then a great range of patient anatomies may be accommodated by providing medial/lateral portions 282 and 284 of various lengths so as to allow for great variation in the inter-rod widths 268.

Placing L-shaped rod 272 which terminates at 256 after a right turn such that the medial/lateral portion 282 is extending laterally from the turn rather than medially as show in FIG. 9 and placing L-shaped rod 274 which terminates at 258 after a left turn so that its medial/lateral portion 284 is extending laterally rather than medially, provides additional options to the surgeon. Placing the L-shaped rods 272 and 274 with the elbows on the medial side allows the inter-rod width 268 to be set to a very small distance so that the cephalad/caudal portions 262 and 264 may interact with structures near the median of the spine.

Connection of Polyaxial Connector Assembly to Occipital Plate.

Figure 11:
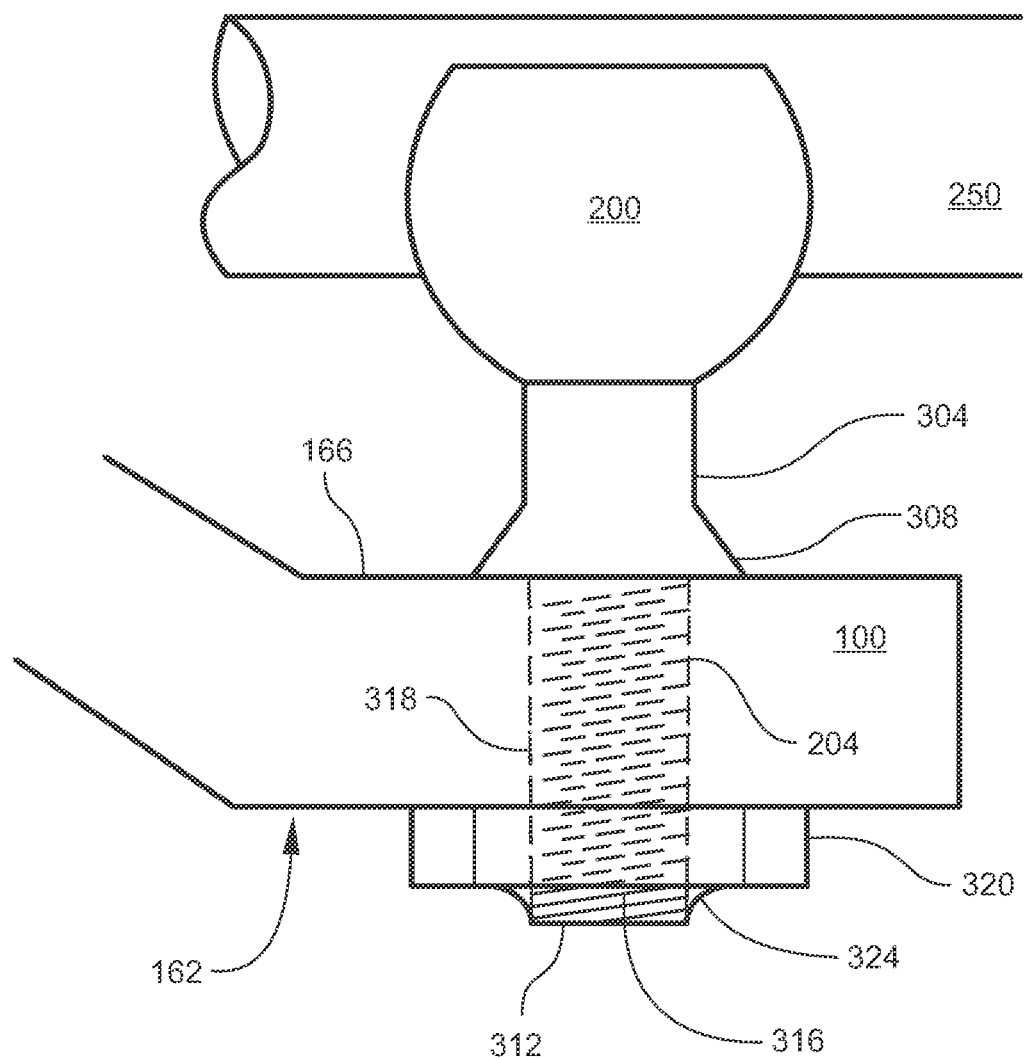
FIG. 11 shows a polyaxial connector assembly 200 with a threaded extension 312 for use in connecting the polyaxial connector assembly 200 to the occipital plate 100.

FIG. 11 shows a polyaxial connector assembly 200 with a threaded extension 312 for use in connecting the polyaxial connector assembly 200 to the occipital plate 100. The polyaxial connector assembly 200 may interact with the spinal rod 250 in the same manner as described above. While the previous drawings introduced a polyaxial connector with an inner split collet and an external collet, those of skill in the art are familiar with many other polyaxial connectors that may lock a rod into position with respect to the polyaxial connector using a set screw, accessory screw, or some other mechanism. Nothing in this disclosure should be interpreted as limiting the teachings of the present disclosure to one particular set of polyaxial connectors. Polyaxial connector assembly 200 may be connected to occipital plate 100 using connector through hole 204. Polyaxial connector assembly 200 has a threaded extension 312 that extends beyond the anterior side 162 of the occipital plate 100. The threaded extension 312 may have machine threads 316 that allow a corresponding nut 320 to be tightened to further pull the posterior shank 304 with machined fillet 308 against the posterior side 166 of the occipital plate 100. Spot welds 324 added after the nut 320 is tightened preclude loosening of the nut 320.

While the first option as listed above has an unthreaded connector through hole 204, an alternative would be to have the machine threads 316 engage with corresponding female threads 318 in the interior of through hole 204. When using an option that engages the machine threads 316 with corresponding female threads 318, the machined fillet 308 may be omitted to allow the machine threads 316 to be advanced through the female threads 318 as desired rather than to seat the machined fillet 308. The diameter of the threaded extension 312 may be made larger along with the diameter of the corresponding connector through hole 204

As shown in FIG. 12, the polyaxial connector assembly 202 may be connected to the occipital plate 100 through use of a connector through hole 204. The polyaxial connector assembly 202 has a shaft 208 sized to be flush with the anterior side 162 of the connector through hole 204 and tack welded into position. The diameter of the shaft 208 may be made larger along with the diameter of the corresponding connector through hole 204.

Alternative Occipital Plates

While it is believed that the occipital plate 100 introduced in FIG. 2 and FIG. 3 will be the appropriate plate for many surgical procedures, alternative occipital plates may be appropriate for certain situations or preferred by some surgeons.

Occipital Plate with Elongated Slots.

FIG. 13 and FIG. 14 show a posterior view and lateral view of an occipital plate 400 with a pair of elongated slots 404 for receipt of a polyaxial connector assembly (not shown). The use of elongated slots 404 provides additional adaptability of the assembly as each polyaxial connector may be translated over the range of the elongated slot 404. The polyaxial connector assembly may be adjusted before the spinal rod 250 (not visible here) is introduced and subsequently adjusted after the spinal rod is introduced but before locking the polyaxial connector assembly to the occipital plate 400. This added adjustability may help in optimal positioning of the head and neck. This added adjustability may be useful in accommodating rod angles with very short radii of curvature. This added adjustability may be useful in reducing the number of different size occipital plates that need to be maintained in inventory to satisfactorily fit most patients.

Other elements in occipital plate 400 are similar to that in occipital plate 100. The through holes 150 may have posterior openings 154 that are larger than the anterior openings 158. The number of through holes 150 may be reduced from the set in occipital plate 100 to allow room for the elongated slots 404.

Like occipital plate 100, occipital plate 400 has an inflection zone 112 between the cephalad end 104 and the caudal end 108 to separate the occipital bony attachment section 134 occipital bony attachment section 134 from the angled connector section 138. Note that the inflection zone 112 for occipital plate 400 is aligned with the most caudal row 412 of through holes 150. Thus, the cable connector section 146 has a second inflection zone 416 at approximately the caudal end 418 of the occipital bony attachment section 134. The cable connector section 146 is shown in FIG. 13 with a cable through hole 148.

Note while FIG. 14 shows a polyaxial connector assembly 420 moved to the cephalad extreme of elongated slot 404 and a polyaxial connector assembly 420 moved to the caudal extreme of elongated slot 404, this is simply to illustrate the range of movement rather than to suggest the use of two polyaxial connectors in the same elongated slot 404.

FIG. 15, FIG. 16, and FIG. 17 show views of polyaxial connector assembly 420 with anterior flange 424 that prevents the polyaxial connector assembly 420 from moving in a posterior direction. These figures do not show a particular locking mechanism for use in affixing the position of the polyaxial connector assembly 420 within the elongated slot 404 of occipital plate 400 but any conventional locking mechanism may be used.

As best seen in FIG. 16, angled connector section 138 is pinned to occipital bony attachment section 134 via pin 408. Thus angled connector section 138 may rotate away from the most caudal end 418 of the occipital bony attachment section 134 by angular deviation 508.

Those of skill in the art will appreciate that the use of a slot to allow for cephalad/caudal motion of the polyaxial connector assembly could be done with an occipital plate without fixed inflection zones (see 112 in FIG. 2). Such an occipital plate may rely on locations with lines of reduced plate thickness 674 to allow the occipital plate to be bent to fit the patient anatomy.

Occipital Plates with Curved Connector Sections.

In occipital plate 100 the angled connector section 138 was substantially flat but at a different angle than the occipital bony attachment section 134 occipital bony attachment section 134. FIG. 18 shows an occipital plate 430 with a connector slot 434 in a curved connector section 438 that is concave with respect to the posterior side 166. In contrast, FIG. 19 shows an occipital plate 440 with a connector slot 444 in a curved connector section 448 that is concave with respect to the anterior side 162. Through the use of a curved connector section, the movement of the polyaxial connector assembly 420 in the connector slot causes a change in both the cephalad/caudal position of the polyaxial connector assembly 420 but also in the anterior/posterior positioning of the polyaxial connector assembly 420 that is different than the movement that may be achieved by an angled connector section with an elongated slot.

Occipital Plate with Hinges.

The occipital plate 100 in FIG. 2 and FIG. 3 shows a fixed angle between the occipital bony attachment section 134 occipital bony attachment section 134 and the angled connector section 138. While it would be possible to stock a set of occipital plates 100 of a given size that differ only in the angle of the angled connector section 138, some surgeons may prefer an occipital plate with an adjustable angle that can locked in place after adjustment to an optimal angle.

Figure 21:
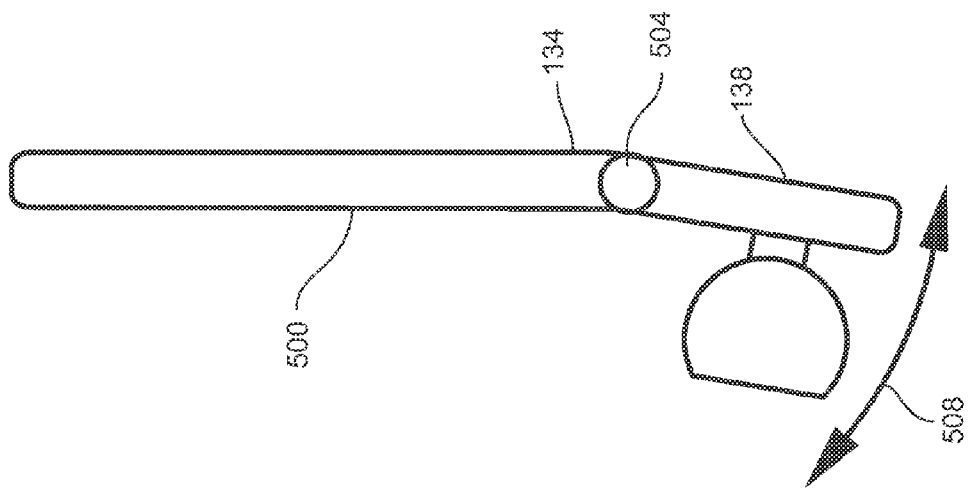
FIG. 21 shows a side view of the occipital plate from FIG. 20.
Figure 20:
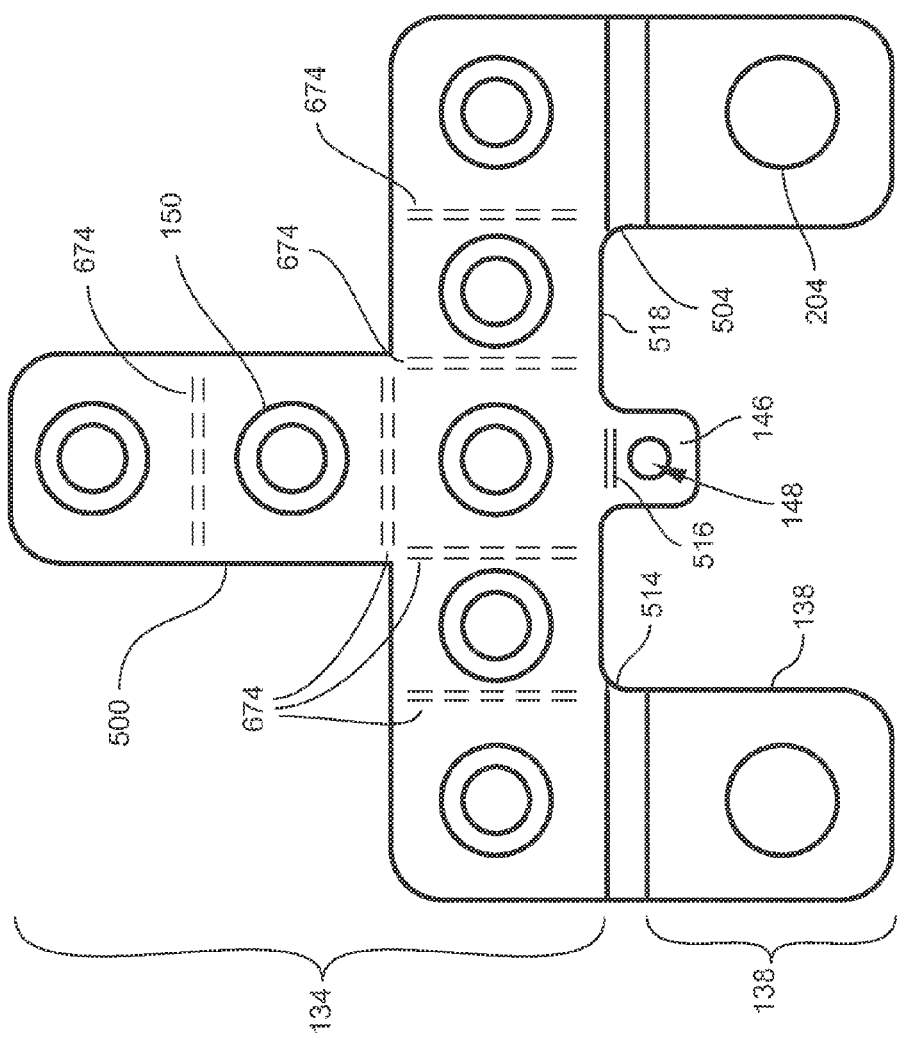
FIG. 20 shows a posterior view of an occipital plate with hinges between the connection section and the occipital bony attachment section.

FIG. 20 shows a posterior view of occipital plate 500 with hinges 504 and 514 between occipital bony attachment section 134 occipital bony attachment section 134 and angled connector section 538. FIG. 21 shows a side view of occipital plate 500. The angular deviation 508 can range from zero degrees up to 60 degrees or more. An occipital plate 500 may support an angular deviation of approximately 90 degrees if desired for some applications.

The cable connector section 146 has a cable through hole 148. The inflection zone 516 for the start of angled movement in the posterior direction of the caudal end of the cable connector section 146 may be in line with the caudal end 518 of the occipital bony attachment section 134. Note that the cable connector section 146 with cable through hole 148 is not hinged but is instead angled at an angle in the range of about twenty to about forty degrees.

The hinges 504 and 514 are independent of one another and may be positioned and locked to have different angular deviations 508. The locking mechanisms for the hinges 504 and 514 are not shown here as they could be any conventional locking mechanism known to those of skill in the art. One of skill in the art will recognize that the use of locking hinges may be combined with the various occipital plates disclosed in this application not just with occipital plate 500. The through holes 150 may the same as described in connection with occipital plate 100 to afford flexibility in delivering screws around the thoracic hump. The polyaxial connector assembly may be connected to connector through hole 204.

Occipital Plate for Use with Cervical Plate.

Referring now to FIG. 22, for some therapeutic procedures, it may be useful to have an occipital plate 550 with an occipital bony attachment section 134 occipital bony attachment section 134 and an angled connector section 138 with a fitting 554 that may receive a connector 570 to allow for a polyaxial connection of a cervical plate 560. After adjusting for the optimal angle of connection between the occipital plate 550 and the cervical plate 560, the connector 570 may be locked into position relative to fitting 554 using any conventional polyaxial locking mechanism. The fitting 554 may be a snap on fitting. The occipital plate 550 having fitting 554 may otherwise have the features of occipital plate 100 discussed above.

Occipital Plate with Maximized Screw Hole Array.

While the occipital plate shown in FIG. 2 and FIG. 3 may be useful in many therapeutic procedures, some patients may require an alternative occipital plate that may be affixed to the skull after a suboccipital craniectomy procedure where the bottom of the skull is removed and thus not available to receive bone screws. Likewise, after discerning that the occipital bone is weak, it may be desirable to have an expanded array of bone screw holes. FIG. 23 and FIG. 24 show a posterior and lateral view of an occipital plate 600. Like occipital plate 100, occipital plate 600 has an occipital bony attachment section 134 occipital bony attachment section 134 and an angled connector section 138 below inflection zone 112. However the layout of the occipital plate 600 and the array of through holes 150 are adapted for this use. The through holes 150 may have the same profile as discussed in connection with occipital plate 100. Polyaxial connector assemblies 200 (not shown here) may be connected using connector through holes 204.

FIG. 25 and FIG. 26 show the posterior and lateral view of occipital plate 620. The occipital plate 620 has a larger array of through holes 150 for insertion of bone screws into the skull to increase the pull out strength of the occipital plate. The through holes 150 may have the same profile as discussed in connection with occipital plate 100. Polyaxial connector assemblies 200 (not shown here) may be connected using connector through holes 204. FIG. 27 shows occipital plate 630 with an even larger array of through holes 150.

Occipital Plate with Mesh Portions.

Referring now to FIG. 28, a posterior view of an occipital plate 640 and FIG. 29, a lateral view of occipital plate 640, in some situations, it may be desirable to use an occipital plate 640 with mesh portions 644. The mesh portions 644 may be used to augment the bone screws delivered via through holes 150. The mesh portions would be sized so that the gaps in the mesh were bigger than the outer diameter of the bone screw but smaller than the head of the screw so that bone screws could be delivered through the mesh to bind the mesh to the skull.

The use of the mesh portions 644 allows the use of multiple locations and multiple screws which may be determined during the medical procedure. Different types of bone screws may be used. The mesh portion 644 may be contoured to better adjust to the patient anatomy relative to an occipital plate such as shown in FIG. 2. Note in an alternative occipital plate not shown, the occipital plate may have mesh portions 644 but not any through holes 150.

The concept of using a mesh portion may be extended for use in a cervical plate 650 as shown in FIG. 28 where occipital plate 640 is connected to cervical plate 650 and to spinal rod 250 to illustrate connection options. The connection between occipital plate 640 and cervical plate 650 may be made using a threaded element 646 and nut 648. FIG. 28 illustrates the use of a polyaxial connector assembly 200 with a spinal rod 250 on one side of occipital plate 640 and a threaded element 646 and nut 648 on the other side of occipital plate 640. While this is a possible configuration, more common configurations would be both sides of occipital plate 640 having polyaxial connector assemblies 200 or both sides of occipital plate 640 having a threaded element 646 to receive cervical plates 650 and nuts 648. Note that when using the pair of polyaxial connector assemblies 200, a unitary spinal rod 252 may be used.

The through holes 150 for occipital plate 640 and variants may the same as described in connection with occipital plate 100 to afford flexibility in delivering screws around the thoracic hump. The polyaxial connector assembly 200 may be connected to connector through hole 204.

Occipital Plates without Midline Bone Screws.

Referring now to FIG. 30 showing the posterior view of an occipital plate 660 and FIG. 31 showing a lateral view of occipital plate 660, occipital plates may be fabricated with a occipital bony attachment section 134 occipital bony attachment section 134, inflection zone 112, and angled connector section 138 for situations where the skull has been removed or otherwise compromised so that bone screws cannot be placed near the midline of the occipital region. While a pair of occipital plates 660 may be used, FIG. 30 also shows an alternative occipital plate 670 which is in an inverted "L" configuration. One of skill in the art will recognize that the inverted "L" could be on the right or left side of the patient, or two inverted "L" occipital plates 670 could be used without an occipital plate 660.

While the inverted "L" shape is demonstrated with occipital plate 670, other variations may include plates with the same array of through holes 150 but including a cross bar to create an H or N shape. Other crossbar configurations may be used to enhance stability.

One of skill in the art will recognize that instead of one cross bar connecting a pair of occipital plates 660, an occipital plate may have two or more cross bars. There may be an advantage of having space above and below and possibly behind a cross member for inserting fusion promoting materials. The cross member may also include:

1) anti-migration features, for example protrusions such as hooks or spikes;
2) anti-slip features, for example surface treatments such as roughening by means of bead-blasting on the anterior surface of the implant as the anterior surface contacts the skull;
3) bone ingrowth features; and
4) combinations of the above.

The through holes 150 for occipital plates 660, 670, and variants may the same as described in connection with occipital plate 100 to afford flexibility in delivering screws around the thoracic hump. The polyaxial connector assembly 200 may be connected to connector through hole 204.

Occipital Plates Adapted to Bending.

An occipital plate may be constructed to have regions of reduced plate thickness in portions of the occipital plate not adjacent to a through hole (150, 204, or 148). The regions of reduced plate thickness may be a line that runs from one side of the occipital plate to the opposite side of the occipital plate. The lines of reduced plate thickness may be used as additional optional inflection points to allow for selected bending of the occipital plate to better conform to patient anatomy. FIG. 2 could include lines of reduced plate thickness at some or all of the locations indicated on FIG. 2 with element number 674. Note that the lines of reduced plate thickness may include a portion of the cable connector section 144 or the angled connector sections 138. The lines of reduced plate thickness 674 may be oriented in the caudal/cephalad axis or in the medial/lateral axis. The use of lines of reduced plate thickness 674 may be used with a variety of occipital plates presented in this disclosure. Accordingly, optional lines of reduced plate thickness are illustrated on many of the occipital plates disclosed to illustrate the many ways that this feature may be used to allow a surgeon to custom fit an occipital plate to a patient's anatomy.

Implant Deployment Tools.

In yet another aspect of the present disclosure, an occipital plate is configured and adapted to be used with straight instruments as opposed to with angled and or articulated tools. The use of non-angled, non-articulating instruments is facilitated when bone fasteners or screws which are inserted into or through the occipital plate from the posterior side to the anterior side and into the skull through an array of holes with centerlines that are angled up to about 60 degrees from perpendicular to the occipital plate surface. The use of straight instruments enables improved line of sight for the surgeon facilitating proper tool placement and intended use thereby avoiding adverse events and adding significantly to patient safety. While the particulars of the tools for deployment of the implants are beyond the focus of this application, the implant deployment tools include drills, drill guides, taps, (screw) drivers, plate holders, rod benders, insertion tools, extraction tools, and tools that may be used for both insertion and extraction.

FIG. 32 illustrates an array of insertion paths from a common point 1010 which is comfortably above the thoracic hump 1014. Insertion paths 1022, 1024, and 1026 may be used for screws that affix the occipital plate 100 to the skull 1018. Note that as insertion paths 1022, 1024, and 1026 are not parallel lines, the insertion angles of the bone screws will not be parallel. This variation in bone screw angle increases pullout strength of the occipital plate 100. Access path 1030 illustrates that the access to cable through hole 148 (see FIG. 2) may be accessed without interference from the thoracic hump 1014.

Component Details.

Materials Choices.

Choices for material for use in the various components comprised in the occipital plate assemblies shown herein are machinable and medical grade, and include but are not limited to titanium or titanium alloys, cobalt-chromium alloys, and stainless steel alloys, or combinations thereof. These biocompatible materials can withstand sterilization techniques such as Ethylene oxide (EtO) gas, radiation, steam autoclaving, dry heat, and cold sterilization. Other desirable attributes are that the material is able to be imaged, e.g., visible via fluoroscopy, X-ray and/or computed tomography (CT); dimensionally stable, and with sufficient biomechanical properties (strength, stiffness, toughness) for intended use, e.g., is sufficiently stiff to allow a relatively thin wall. If needed, materials may be used with incorporated with fluoroscopic visualization markers, for example, tantalum, although other materials may be used. For some occipital plate assemblies, the selected material(s) is preferably able to undergo surface treatments, such as bead blasting, to promote anti-slippage of the plate in contact with the skull.

The materials chosen will be biocompatible which refers to an absence of chronic inflammation response or cytotoxicity when or if physiological tissues are in contact with, or exposed to the materials and devices of the present disclosure. Certain components of the occipital plate assemblies of the present disclosure are configured to comprise biocompatible materials and are able to withstand, without significant wear, multiple cycles of use such as placement and removal from a patient without failing.

Provision of Therapy after Creating Access.

After creating access first to the occiput and then to the targeted posterior spinal vertebral levels, and aligning and stabilizing/fixing them using the methods known to those of skill in the art, a portion of the skull and/or spine may be accessed for the provision of additional therapy.

One form of therapy is to fuse the occiput and selected spinal levels together. Spinal fusion typically involves the use of osteogenic, osteoconductive, or osteoinductive material (bone graft and or bone graft substitutes). One process to promote fusion is to insert quantities of one or more fusion promoting materials into the areas to be fused. Bone graft is the material that is used to promote bone growth and forms the scaffold that bridges the adjacent vertebral bodies comprising a motion segment in the spine, and vertebrae to the skull. Once healed, the fused portions of the skull and vertebrae do not move with respect to one another.

It is useful to have one name for the variety of materials used to promote fusion. Thus, fusion promoting materials including osteogenic, osteoconductive, and/or osteoinductive material are collectively described herein as "bone graft material", whether the material is autograft or allograft and various bone graft substitutes or bone graft extenders. Various techniques for promoting effective fusion of adjacent vertebrae are well known to those of skill in the art so a minimal summary is sufficient for this document.

Size Ranges.

The dimensions of the occipital plate implants will be, in part, a function of the patient anatomy as well as the condition (e.g., depth, strength) of available bone of the occiput. That is, dimensions (e.g., height, width, thickness) of the implants will be a function of the size of the patient as some patients have larger bones than other patients. Thus, the plate may be scaled to fit adults of smaller stature, e.g., the anterior to posterior dimension and the lateral dimension will vary based on the size of the relevant target site. The height of the implant may also be selected to match the surgeon's preference for the spacing of the implant on the skull. In general, the height of the occipital plate implants of the present disclosure range from between about 36 mm and about 56 mm and often about 42 mm to about 46 mm, with widths from between about 36 mm and about 56 mm, and with thicknesses (between posterior surface and anterior surface of occipital plate) of between about 1 mm and about 3 mm. The thickness of the occipital plate may be reduced in certain areas in order to facilitate bending or contouring.

The occipital plate should be sized and contoured to lie smoothly against the occiput. In may be necessary to smooth irregular bony protuberances to optimize the bone to plate interface, but care should be taken to avoid removing significant portions of cortical bone especially in the vicinity of planned screw holes. It is also preferred that the plate dimensions allow for adequate volume of bone graft to be deployed near the foramen magnum caudal to the implant. The occipital plate may be used in conjunction with bone graft types that are autologous or allogeneic, e.g., grafts from the iliac crest, rib, occiput, or tibia/fibula donor sites of the patient or cadaveric donor. As noted above, the bone graft material may include bone graft substitutes. Autograft, a combination of autograft and allograft, or allograft alone may be used.

Overview of Surgical Process to Use Occipital Plates.

Given the description of the various occipital plates within this disclosure, the process for using the surgical plates may be summarized as follows.

A method of fusing a portion of a skull to a portion of a spine, the method comprising:

surgically accessing and exposing the portion of the skull and the portion of the spine to be fused;

providing an occipital plate configured to contact a region of the skull and be secured threreto, the occipital plate having:

a posterior surface;

an anterior surface opposite the posterior surface for placement adjacent the region of the skull when the occipital plate is secured thereto;

a side surface between the posterior surface and the anterior surface;

a plurality of bone fastener holes wherein each bone fastener hole is configured and dimensioned to receive a bone fastener deployed by a set of at least one non-angled and non-articulated instrument;

at least one angled connector section configured and dimensioned to engage a polyaxial connector assembly adapted to adjustably receive and secure an elongate spinal rod that connects to the occipital plate to an at least one vertebral connector attached to the portion of the spine to by fused with the portion of the skull thereby forming an implant construct; and at least one cable through hole adapted to engage and secure a leading end of a tension cable;

contouring and then fixing the occipital plate to the portion of the skull by inserting bone fasteners through the bone fastener holes in the occipital plate and into the region of the skull;

inserting a plurality of vertebral connectors into the portion of the spine to be fused to the portion of the skull;

applying each of a set of at least one tension cable by inserting and securing the leading end of the tension cable to one of the at least one cable through hole;

inserting a trailing end of each of the set of at least one tension cable into one of the plurality of vertebral connectors;

tensioning each tension cable to obtain optimal lordosis and alignment and to secure any structural bone graft and securing each tension cable to the implant construct;

inserting a leading end of the spinal rod into the polyaxial connector assembly and optimizing sagittal and coronal alignment by making adjustments by at least one movement in a translational, rotational, cephalad-caudal, or medial-lateral direction; of a position of the spinal rod relative to the occipital plate and an inter-rod width between the spinal rod and another spinal rod;

mechanically securing the spinal rod in the polyaxial connector assembly;

contouring the spinal rod and positionally fixing the occipital plate and spinal rod by connecting at least one intermediate portion of the spinal rod with at least one vertebral connector and connecting a trailing end of the spinal rod into another vertebral connector; and inserting bone growth media into the portion of the skull and the portion of the spine to be fused.

In some instances after into the area to be fused, the surgeon may wish to make final adjustments to the assembly before closing the surgical site.

The process may use one occipital plate with a pair of polyaxial assemblies and a pair of spinal rods. The process may use a pair of occipital plates each having a polyaxial connector assembly for receipt of a spinal rod. Two different polyaxial assemblies may engage a unitary rod. The use of L-shaped rods may be used to provide the surgeon with a range of options for setting an inter-rod width between the spinal rods so as to allow use of the spinal rods with a range of patient anatomies and connection choices to different portions of the vertebrae.

Alternatively, as noted above the process may be modified to connect an occipital plate with at least one threaded connection to a cervical plate. Thus, variations of the process include connecting an occipital plate to cervical plates as well as cervical rods, or combinations thereof, which may extend to more caudal spinal levels.

Multi-Level Surgery.

While for convenience, the description set forth above focused on providing therapy to fixation of the skull relative to cervical motion segments (i.e., one disc space between two adjacent vertebrae), one of skill in the art will recognize that the process set forth above may applied to assemblies so that more than one motion segment, in other spinal levels, e.g., thoracic, and lumbosacral receives therapy (such as fusion) during a single surgical intervention.

Open Surgery

While the focus of this disclosure has been on an open surgery posterior access approach to the skull and spine, the various implants described in this application may be used with other access routes including a minimally invasive rather than an open approach.

Kits.

One of skill in the art will recognize that the surgical procedures set forth above may benefit from various kits of tools and components for use in these procedures. Kits may focus on reusable or disposable components for creating an access route. Other kits may focus on the tools for preparing the targeted surgical site(s). A kit may include many (possibly even all) the components necessary for a particular procedure including the components needed to create the access route, prepare the targeted sites and even an assortment of implants, as well as the instruments needed for their deployment.

As the instrument sets will tend to be sterilized and reused for subsequent procedures, a kit may include the various components and alternatives that may be connected to the patient during the surgical procedure. Thus, the kit may include a variety of occipital plates. The occipital plates may differ in size, shape, the number and arrangement of through holes for the bone screws, including potentially some occipital plates using mesh portions (see 644 above). Some occipital plates may have lines of reduced plate thickness to allow for the occipital plate to be bent for an improved fit.

The occipital plates will normally come with one or more polyaxial connector assemblies already affixed to the occipital plate. Axial rods compatible with the polyaxial connector assemblies or cervical plates may be provided in the kit. The kit may include cables and or tape that may be used with the cable through holes 148. The kit may include bone screws for use in affixing the occipital plate to the skull.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples provided to promote understanding of the various teachings of the present disclosure. Moreover, the scope of the claims which follow covers the range of variations, modifications, and substitutes for the components described herein as would be known to those of skill in the art. Individual claims may be tailored to claim particular examples out of the array of examples disclosed above. Some claims may be tailored to claim alternative examples rather than preferred examples. Some claims may cover a variation set forth above with a modification from another example as the present disclosure does not include drawings of all possible combinations of feature sets.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. An occipital plate comprising:
    an attachment section having a plurality of through holes for securing the occipital plate to a portion of a skull;
    first and second inflection zones extending from the attachment section, the first and second inflection zones being laterally spaced apart and defining a gap therebetween;
    first and second connector sections coupled to respective first and second inflection zones, the first and second connector sections independently adjustable such that the first connector section defines a first angle with respect to the attachment section and the second connector section defines a second angle with respect to the attachment section; and
    first and second polyaxial connector assemblies connected to respective first and second connector sections, each polyaxial connector assembly movable to adjust an orientation of an opening of the polyaxial connector assembly, wherein each polyaxial connector assembly includes a threaded element insertable into bone.

2. The occipital plate of claim 1, wherein the occipital plate further includes:
    a midline with the first and second polyaxial connector assemblies on opposing sides of the midline; and
    a cable connector section disposed along the midline and located caudally of the first and second inflection zones.

3. The occipital plate of claim 2, wherein the cable connector section is coupled to the attachment section via a third inflection zone such that the cable connector section is independently adjustable relative to the attachment section and one of the connector sections.

4. The occipital plate of claim 2, further including a plurality of cable through holes.

5. The occipital plate of claim 1, wherein the first polyaxial connector assembly is transitionable between a first mode and a second mode, the first polyaxial connector assembly disposed in an elongated slot and slidable along the cephalad/caudad axis when in the first mode and in a fixed position in the elongate slot when in the second mode.

6. The occipital plate of claim 1, wherein the first and second connector sections are adjustable along an anterior/posterior axis.

7. The occipital plate of claim 6, wherein one of the inflection zones includes a lockable hinge such that the associated connecter section is securable in a fixed angular orientation with respect to the attachment section.

8. The occipital plate of claim 1, wherein the occipital plate has a line of reduced plate thickness oriented in a medial-lateral direction and a line of reduced plate thickness oriented in a caudad-cephalad direction.

9. The occipital plate of claim 1, wherein the first angle is different from the second angle.

10. A method for affixing an occipital plate to an occipital region of a skull comprising:
    securing an attachment section of the occipital plate to the occipital region of the skull;
    engaging a first polyaxial connector assembly of the occipital plate with a spinal rod, the spinal rod connected to a component anchored in a spine;
    locking the first polyaxial connector assembly to fix a position of the spinal rod with respect to the first polyaxial connector assembly; and
    adjusting an orientation of a first connector section relative to the attachment section, the adjustment being in an anterior-posterior direction, wherein the attachment section includes a lockable hinge coupling the first connector section to the attachment section.

11. The method of claim 10, further including adjusting an orientation of a second connector section relative to the attachment section, the adjustment being in the anterior-posterior direction.

12. The method of claim 11, wherein adjusting the orientation of the second connector section includes the orientation of the first connector section being different from the orientation of the second connector section.

13. The method of claim 11, wherein adjusting the orientation of the first connector section and adjusting the orientation of the second connector section includes the first connector section disposed on a first side of a midline of the occipital plate and the second connector section disposed on a second side of the midline.

14. The method of claim 10, further including:
moving the first polyaxial connector assembly in an elongated slot of the occipital plate assembly with the first polyaxial connector assembly in a first mode before locking the first polyaxial connector assembly by transitioning the first polyaxial connector assembly to a second mode.

15. The method of claim 10, wherein adjusting an orientation of the first connector section includes an inflection zone disposed between the first connector section and the attachment section.

16. The method of claim 10, further including locking the lockable hinge to fix a position of the first connector section relative to the attachment section.

17. The method of claim 10, further including:
connecting a cable to a cable connection section of the occipital plate, the cable connection section disposed along a midline of the occipital plate and caudal of an inflection zone of the occipital plate; and
imparting tension between the cable connection section and an anchored caudal end of the cable.

18. A method of fusing a portion of a skull to a portion of a spine comprising:
surgically accessing and exposing the portion of the skull and the portion of the spine to be fused;
contouring an occipital plate to the portion of the skull;
fixing the occipital plate to the portion of the skull by inserting bone fasteners through bone fastener holes in the occipital plate and into the portion of the skull;
inserting a plurality of vertebral connectors into the portion of the spine to be fused to the portion of the skull;
inserting a leading end of a tension cable through a cable through hole of the occipital plate:
securing the leading end of the tension cable to the cable through hole;
inserting a trailing end of the tension cable into one vertebral connector of the plurality of vertebral connectors;
tensioning the tension cable to obtain a desired amount of lordosis and alignment;
inserting a leading end of a spinal rod into a polyaxial connector assembly of the occipital plate;
adjusting the spinal rod by movement in a translational, rotational, cephalad-caudad, or medial-lateral direction relative to the occipital plate to affect sagittal or coronal alignment;
mechanically securing the spinal rod in the polyaxial connector assembly;
contouring the spinal rod and positionally fixing the occipital plate and spinal rod by connecting at least one intermediate portion of the spinal rod with at least one vertebral connector and connecting a trailing end of the spinal rod into another vertebral connector; and
inserting bone growth media into the portion of the skull and the portion of the spine to be fused.

19. An occipital plate comprising:
an attachment section having a plurality of through holes for securing the occipital plate to a portion of a skull;
first and second inflection zones extending from the attachment section, the first and second inflection zones being laterally spaced apart and defining a gap therebetween;
first and second connector sections coupled to respective first and second inflection zones, the first and second connector sections independently adjustable such that the first connector section defines a first angle with respect to the attachment section and the second connector section defines a second angle with respect to the attachment section;
first and second polyaxial connector assemblies connected to respective first and second connector sections, each polyaxial connector assembly movable to adjust an orientation of an opening of the polyaxial connector assembly;
a midline with the first and second polyaxial connector assemblies on opposing sides of the midline; and
a cable connector section disposed along the midline and located caudally of the first and second inflection zones.

20. A method for affixing an occipital plate to an occipital region of a skull comprising:
securing an attachment section of the occipital plate to the occipital region of the skull;
engaging a first polyaxial connector assembly of the occipital plate with a spinal rod, the spinal rod connected to a component anchored in a spine;
locking the first polyaxial connector assembly to fix a position of the spinal rod with respect to the first polyaxial connector assembly;
adjusting an orientation of a first connector section relative to the attachment section, the adjustment being in an anterior-posterior direction;
connecting a cable to a cable connection section of the occipital plate, the cable connection section disposed along a midline of the occipital plate and caudal of an inflection zone of the occipital plate; and
imparting tension between the cable connection section and an anchored caudal end of the cable.

* * * * *